(12) United States Patent
Marmo et al.

(10) Patent No.: US 7,828,844 B2
(45) Date of Patent: Nov. 9, 2010

(54) INSERTING LENSES INTO CORNEAL EPITHELIAL POCKETS TO IMPROVE VISION

(75) Inventors: J. Christopher Marmo, Danville, CA (US); Arthur Back, Danville, CA (US); Greg S. Hollrigel, San Clemente, CA (US)

(73) Assignee: ForSight Labs, LLC, Menlo Park, CA (US)

( * ) Notice: Subject to any disclaimer, the term of this patent is extended or adjusted under 35 U.S.C. 154(b) by 115 days.

(21) Appl. No.: 10/661,400

(22) Filed: Sep. 12, 2003

(65) Prior Publication Data

US 2005/0080484 A1    Apr. 14, 2005

Related U.S. Application Data

(60) Provisional application No. 60/464,590, filed on Apr. 21, 2003, provisional application No. 60/464,004, filed on Apr. 18, 2003, provisional application No. 60/410,837, filed on Sep. 13, 2002.

(51) Int. Cl.
    *A61F 2/14*    (2006.01)
(52) U.S. Cl. .................. 623/5.11; 623/5.14; 623/906
(58) Field of Classification Search ............... 623/5.11, 623/5.14, 5.16, 906
    See application file for complete search history.

(56) References Cited

U.S. PATENT DOCUMENTS

| | | | |
|---|---|---|---|
| 1,569,707 A * | 1/1926 | Bunnell .................. 298/16 |
| 1,999,286 A * | 4/1935 | De Bolt et al. .............. 188/335 |
| 2,134,744 A * | 11/1938 | Wales ..................... 192/107 M |
| 2,227,827 A * | 1/1941 | Dubar ........................ 438/102 |
| 2,286,718 A * | 6/1942 | Curtis ......................... 560/19 |
| 3,361,200 A * | 1/1968 | Chambers ................... 166/343 |
| 4,078,564 A * | 3/1978 | Spina et al. ................. 604/506 |
| 4,126,904 A * | 11/1978 | Shepard .................... 623/5.15 |
| 4,223,984 A * | 9/1980 | Miyata et al. ........... 351/160 H |
| 4,268,131 A * | 5/1981 | Miyata et al. ........... 351/160 H |
| 4,346,482 A * | 8/1982 | Tennant et al. ............. 623/5.15 |

(Continued)

FOREIGN PATENT DOCUMENTS

CA    2134744    5/1995

(Continued)

OTHER PUBLICATIONS

Tsai et al., "Reconstruction of damaged corneas by transplantation of autologous limbal epithelial cells", The New England Journal of Medicine, vol. 343 #2, p. 86-93, Jul. 13, 2000.

(Continued)

*Primary Examiner*—Paul Prebilic
(74) *Attorney, Agent, or Firm*—Townsend and Townsend and Crew LLP

(57) ABSTRACT

Methods of correcting vision are described. The methods include inserting a lens into a corneal epithelial pocket or a pocket created between a corneal epithelium of an eye of a patient and Bowman's membrane of the eye. A lens is inserted into the pocket to correct vision. Certain methods include one or more steps of cooling the corneal epithelium, and applying an aqueous liquid to the eye. The lenses that are inserted into the pocket can include collagen, including recombinant collagen, synthetic polymeric materials, and combinations thereof.

109 Claims, 12 Drawing Sheets

U.S. PATENT DOCUMENTS

| | | | | |
|---|---|---|---|---|
| 4,452,235 A * | 6/1984 | Reynolds | | 128/898 |
| 4,452,776 A * | 6/1984 | Refojo | | 514/772.4 |
| 4,452,925 A * | 6/1984 | Kuzma et al. | | 523/106 |
| 4,563,779 A * | 1/1986 | Kelman | | 623/5.16 |
| 4,581,030 A * | 4/1986 | Bruns et al. | | 623/5.16 |
| 4,600,533 A * | 7/1986 | Chu | | 530/356 |
| 4,619,257 A * | 10/1986 | Linner et al. | | 606/20 |
| 4,619,657 A * | 10/1986 | Keates et al. | | 623/6.4 |
| 4,621,912 A * | 11/1986 | Meyer | | 351/160 R |
| 4,624,669 A * | 11/1986 | Grendahl | | 623/5.13 |
| 4,636,210 A * | 1/1987 | Hoffer | | 623/6.2 |
| 4,655,774 A * | 4/1987 | Choyce | | 623/5.11 |
| 4,655,980 A * | 4/1987 | Chu | | 264/102 |
| 4,676,790 A * | 6/1987 | Kern | | 128/898 |
| 4,689,399 A * | 8/1987 | Chu | | 530/356 |
| 4,693,715 A * | 9/1987 | Abel, Jr. | | 623/5.15 |
| 4,715,858 A * | 12/1987 | Lindstrom | | 623/5.13 |
| 4,725,671 A * | 2/1988 | Chu et al. | | 530/356 |
| 4,780,409 A | 10/1988 | Monji et al. | | |
| 4,784,485 A * | 11/1988 | Ho | | 356/124 |
| 4,799,931 A * | 1/1989 | Lindstrom | | 623/5.13 |
| 4,810,082 A * | 3/1989 | Abel, Jr. | | 351/160 R |
| 4,819,617 A * | 4/1989 | Goldberg et al. | | 128/897 |
| 4,834,748 A * | 5/1989 | McDonald | | 128/898 |
| 4,851,003 A * | 7/1989 | Lindstrom | | 623/5.13 |
| 4,923,467 A * | 5/1990 | Thompson | | 128/898 |
| 4,952,212 A * | 8/1990 | Booth et al. | | 604/294 |
| 4,959,353 A * | 9/1990 | Brown et al. | | 514/12 |
| 4,973,493 A * | 11/1990 | Guire | | 427/2.24 |
| 4,978,713 A * | 12/1990 | Goldenberg | | 525/61 |
| 4,979,959 A * | 12/1990 | Guire | | 435/176 |
| 4,981,841 A * | 1/1991 | Gibson | | 514/2 |
| 4,983,181 A * | 1/1991 | Civerchia | | 623/5.11 |
| 4,994,081 A * | 2/1991 | Civerchia et al. | | 606/107 |
| 5,019,097 A * | 5/1991 | Knight et al. | | 623/5.13 |
| 5,044,743 A | 9/1991 | Ting | | |
| 5,104,408 A * | 4/1992 | Thompson | | 128/898 |
| 5,108,428 A * | 4/1992 | Capecchi et al. | | 623/5.16 |
| 5,112,350 A * | 5/1992 | Civerchia et al. | | 606/107 |
| 5,114,627 A * | 5/1992 | Civerchia | | 264/1.1 |
| 5,151,310 A * | 9/1992 | Yanagisawa et al. | | 428/64.8 |
| 5,156,622 A * | 10/1992 | Thompson | | 128/898 |
| 5,163,956 A * | 11/1992 | Liu et al. | | 623/4.1 |
| 5,171,318 A * | 12/1992 | Gibson et al. | | 623/5.16 |
| 5,192,316 A * | 3/1993 | Ting | | 623/5.16 |
| 5,196,026 A * | 3/1993 | Barrett et al. | | 128/898 |
| 5,196,027 A * | 3/1993 | Thompson et al. | | 128/898 |
| 5,201,764 A * | 4/1993 | Kelman et al. | | 623/6.59 |
| 5,213,720 A * | 5/1993 | Civerchia | | 264/1.38 |
| 5,244,799 A * | 9/1993 | Anderson | | 435/397 |
| 5,263,992 A * | 11/1993 | Guire | | 623/66.1 |
| 5,288,436 A * | 2/1994 | Liu et al. | | 264/1.38 |
| 5,292,514 A * | 3/1994 | Capecchi et al. | | 424/422 |
| 5,300,118 A * | 4/1994 | Silvestrini et al. | | 623/5.12 |
| 5,330,911 A | 7/1994 | Hubbell et al. | | |
| 5,395,385 A * | 3/1995 | Kilmer et al. | | 606/166 |
| 5,401,508 A * | 3/1995 | Manesis | | 424/427 |
| 5,433,745 A | 7/1995 | Graham et al. | | |
| 5,443,473 A * | 8/1995 | Miller et al. | | 606/174 |
| 5,470,831 A | 11/1995 | Whitman et al. | | |
| 5,475,052 A * | 12/1995 | Rhee et al. | | 525/54.1 |
| 5,489,300 A * | 2/1996 | Capecchi et al. | | 128/898 |
| 5,496,339 A * | 3/1996 | Koepnick | | 606/166 |
| 5,522,888 A * | 6/1996 | Civerchia | | 623/5.16 |
| 5,547,468 A * | 8/1996 | Simon et al. | | 604/21 |
| 5,552,452 A * | 9/1996 | Khadem et al. | | 522/63 |
| 5,565,519 A * | 10/1996 | Rhee et al. | | 525/54.1 |
| 5,587,175 A * | 12/1996 | Viegas et al. | | 424/427 |
| 5,614,587 A * | 3/1997 | Rhee et al. | | 525/54.1 |
| 5,632,773 A * | 5/1997 | Graham et al. | | 623/6.61 |
| 5,690,657 A * | 11/1997 | Koepnick | | 606/166 |
| 5,713,957 A | 2/1998 | Steele et al. | | |
| 5,716,633 A * | 2/1998 | Civerchia | | 424/428 |
| 5,722,971 A | 3/1998 | Peyman | | |
| 5,744,545 A * | 4/1998 | Rhee et al. | | 525/54.1 |
| 5,800,541 A * | 9/1998 | Rhee et al. | | 424/423 |
| 5,827,641 A | 10/1998 | Parenteau et al. | | |
| 5,832,313 A * | 11/1998 | Ishibashi et al. | | 396/79 |
| 5,836,313 A | 11/1998 | Perez et al. | | |
| 5,919,185 A | 7/1999 | Peyman | | |
| 5,964,748 A | 10/1999 | Peyman | | |
| 5,984,914 A * | 11/1999 | Cumming | | 606/4 |
| 5,994,133 A * | 11/1999 | Meijs et al. | | 435/395 |
| 6,015,609 A * | 1/2000 | Chaouk et al. | | 428/308.4 |
| 6,030,634 A | 2/2000 | Wu et al. | | |
| 6,055,990 A * | 5/2000 | Thompson | | 128/898 |
| 6,060,530 A * | 5/2000 | Chaouk et al. | | 521/64 |
| 6,063,073 A | 5/2000 | Peyman | | |
| 6,071,293 A * | 6/2000 | Krumeich | | 606/166 |
| 6,086,204 A * | 7/2000 | Magnante | | 351/212 |
| 6,090,995 A * | 7/2000 | Reich et al. | | 623/23.76 |
| 6,099,541 A * | 8/2000 | Klopotek | | 606/166 |
| 6,103,528 A | 8/2000 | An et al. | | |
| 6,165,488 A * | 12/2000 | Tardy et al. | | 424/426 |
| 6,186,148 B1 * | 2/2001 | Okada | | 128/898 |
| 6,197,019 B1 | 3/2001 | Peyman | | |
| 6,203,538 B1 | 3/2001 | Peyman | | |
| 6,217,571 B1 | 4/2001 | Peyman | | |
| 6,221,067 B1 | 4/2001 | Peyman | | |
| 6,241,766 B1 * | 6/2001 | Liao et al. | | 623/6.56 |
| 6,271,278 B1 | 8/2001 | Park et al. | | |
| 6,280,470 B1 | 8/2001 | Peyman | | |
| 6,284,537 B1 | 9/2001 | Offord Cavin et al. | | |
| 6,323,278 B2 | 11/2001 | Rhee et al. | | |
| 6,335,006 B1 * | 1/2002 | Miller | | 424/78.04 |
| 6,361,560 B1 | 3/2002 | Nigam | | |
| 6,384,105 B1 | 5/2002 | He et al. | | |
| 6,388,047 B1 | 5/2002 | Won et al. | | |
| 6,454,800 B2 * | 9/2002 | Dalton et al. | | 623/5.11 |
| 6,454,802 B1 | 9/2002 | Bretton et al. | | |
| 6,511,949 B1 * | 1/2003 | Nitta et al. | | 510/112 |
| 6,544,286 B1 | 4/2003 | Perez | | |
| 6,547,391 B2 * | 4/2003 | Ross et al. | | 351/212 |
| 6,551,307 B2 | 4/2003 | Peyman | | |
| 6,566,406 B1 | 5/2003 | Pathak et al. | | |
| 6,579,918 B1 * | 6/2003 | Auten et al. | | 523/106 |
| 6,585,375 B2 | 7/2003 | Donitzky | | |
| 6,607,522 B1 * | 8/2003 | Hamblin et al. | | 606/8 |
| 6,645,715 B1 * | 11/2003 | Griffith et al. | | 435/1.1 |
| 6,689,165 B2 * | 2/2004 | Jacob et al. | | 623/5.16 |
| 6,702,807 B2 * | 3/2004 | Peyman | | 606/5 |
| 6,717,651 B2 * | 4/2004 | Kato et al. | | 355/55 |
| 6,855,163 B2 * | 2/2005 | Peyman | | 623/5.11 |
| 6,880,558 B2 * | 4/2005 | Perez | | 128/898 |
| 6,897,064 B2 | 5/2005 | Yoshioka et al. | | |
| 6,918,904 B1 * | 7/2005 | Peyman | | 606/5 |
| 7,004,953 B2 * | 2/2006 | Pallikaris et al. | | 606/166 |
| 7,008,447 B2 * | 3/2006 | Koziol | | 623/5.11 |
| 7,053,051 B2 * | 5/2006 | Hendriks et al. | | 514/12 |
| 7,077,839 B2 * | 7/2006 | Hamblin et al. | | 606/8 |
| 7,156,859 B2 * | 1/2007 | Pallikaris et al. | | 606/166 |
| 7,166,118 B2 * | 1/2007 | Dame et al. | | 606/166 |
| 7,207,998 B2 * | 4/2007 | Feingold | | 606/166 |
| 2001/0018612 A1 * | 8/2001 | Carson et al. | | 623/5.11 |
| 2001/0027314 A1 | 10/2001 | Peyman | | |
| 2001/0034516 A1 | 10/2001 | Peyman | | |
| 2001/0047203 A1 * | 11/2001 | Dalton et al. | | 623/5.13 |
| 2002/0007217 A1 | 1/2002 | Jacob et al. | | |
| 2002/0022013 A1 * | 2/2002 | Leukel et al. | | 424/78.17 |
| 2002/0039788 A1 | 4/2002 | Isseroff et al. | | |
| 2002/0052596 A1 | 5/2002 | Pallikaris et al. | | |
| 2002/0052615 A1 * | 5/2002 | Ross et al. | | 606/166 |
| 2002/0055753 A1 | 5/2002 | Silvestrini | | |
| 2002/0065555 A1 | 5/2002 | Nigam | | |

| | | | | | | | |
|---|---|---|---|---|---|---|---|
| 2002/0071097 | A1* | 6/2002 | Ross et al. ............... 351/212 | WO | WO 2005/049071 A2 | 6/2005 | |
| 2002/0138069 | A1 | 9/2002 | Peyman | WO | WO 2005/116729 | 12/2005 | |
| 2003/0018123 | A1* | 1/2003 | Bagrov et al. ............ 525/54.11 | WO | WO 2006/007408 | 1/2006 | |
| 2003/0018347 | A1 | 1/2003 | Pallikaris et al. | WO | WO 2006/015490 | 2/2006 | |
| 2003/0018348 | A1 | 1/2003 | Pallikaris et al. | WO | WO 2006/020859 A2 | 2/2006 | |
| 2003/0093083 | A1 | 5/2003 | Peyman | WO | WO 2006/116601 | 11/2006 | |
| 2003/0105521 | A1* | 6/2003 | Perez ....................... 623/5.16 | WO | WO 2006/116732 | 11/2006 | |
| 2003/0220653 | A1* | 11/2003 | Perez ....................... 606/107 | WO | WO 2007/028258 | 3/2007 | |
| 2004/0015234 | A1 | 1/2004 | Peyman | | | | |
| 2004/0046287 | A1* | 3/2004 | Andino et al. ............. 264/401 | | | | |
| 2004/0075807 | A1* | 4/2004 | Ho et al. ................. 351/160 R | | | | |
| 2004/0125459 | A1* | 7/2004 | Tanitsu et al. ............... 359/619 | | | | |
| 2004/0142038 | A1* | 7/2004 | Echols et al. ............. 424/486 | | | | |
| 2004/0170666 | A1* | 9/2004 | Keates et al. ............... 424/428 | | | | |
| 2004/0183998 | A1* | 9/2004 | Luce ....................... 351/212 | | | | |
| 2004/0243160 | A1* | 12/2004 | Shiuey et al. ............. 606/166 | | | | |
| 2005/0070942 | A1* | 3/2005 | Perez ....................... 606/166 | | | | |
| 2005/0080484 | A1* | 4/2005 | Marmo et al. ............. 623/5.14 | | | | |
| 2005/0124982 | A1* | 6/2005 | Perez ....................... 606/4 | | | | |
| 2005/0196427 | A1* | 9/2005 | Tirrell et al. ............... 424/427 | | | | |
| 2005/0251185 | A1* | 11/2005 | Gebauer .................... 606/166 | | | | |
| 2005/0259221 | A1* | 11/2005 | Marmo .................... 351/160 R | | | | |
| 2006/0034807 | A1* | 2/2006 | Griffith ..................... 424/93.7 | | | | |
| 2006/0052796 | A1* | 3/2006 | Perez et al. ................ 606/107 | | | | |
| 2006/0064112 | A1* | 3/2006 | Perez ....................... 606/107 | | | | |
| 2006/0071356 | A1* | 4/2006 | Beebe ....................... 264/2.2 | | | | |
| 2006/0134050 | A1* | 6/2006 | Griffith et al. ............. 424/70.16 | | | | |
| 2006/0134170 | A1* | 6/2006 | Griffith et al. ............. 424/427 | | | | |
| 2006/0190004 | A1* | 8/2006 | Dick et al. ................. 606/108 | | | | |
| 2006/0241751 | A1* | 10/2006 | Marmo et al. ............. 623/5.11 | | | | |
| 2006/0246113 | A1* | 11/2006 | Griffith et al. ............. 424/427 | | | | |
| 2006/0247660 | A1* | 11/2006 | Perez ....................... 606/107 | | | | |
| 2007/0016292 | A1* | 1/2007 | Perez ....................... 623/5.13 | | | | |
| 2007/0026046 | A1 | 2/2007 | Fogg et al. | | | | |
| 2007/0182920 | A1* | 8/2007 | Back et al. ............... 351/160 R | | | | |
| 2007/0239184 | A1* | 10/2007 | Gaeckle et al. ............. 606/166 | | | | |
| 2007/0265649 | A1 | 11/2007 | Perez | | | | |
| 2008/0024723 | A1 | 1/2008 | Marmo | | | | |
| 2008/0269119 | A1* | 10/2008 | Griffith et al. ................ 514/12 | | | | |

FOREIGN PATENT DOCUMENTS

| | | |
|---|---|---|
| CA | 2286718 | 11/1998 |
| CA | 2227827 | 7/1999 |
| DE | 199 47 711 | 5/2001 |
| EP | 0 387 975 | 3/1990 |
| EP | 1 530 600 B1 | 5/2005 |
| EP | 1 741 457 A1 | 1/2007 |
| GB | 1 569 707 | 6/1980 |
| GB | 2305608 | 4/1997 |
| WO | WO 88/02622 | 4/1988 |
| WO | WO 92/14420 | 9/1992 |
| WO | WO 93/07889 | 4/1993 |
| WO | WO 94/16570 | 8/1994 |
| WO | WO 94/17851 | 8/1994 |
| WO | WO 95/13764 | 5/1995 |
| WO | WO 98/03267 | 1/1998 |
| WO | WO 98/31316 | 7/1998 |
| WO | WO 99/37752 | 7/1999 |
| WO | WO 00/07525 | 2/2000 |
| WO | WO 00/35524 | 6/2000 |
| WO | WO 00/67694 | 11/2000 |
| WO | WO 02/06883 | 1/2002 |
| WO | WO 02/06883 A2 * | 1/2002 |
| WO | WO 02/092142 | 11/2002 |
| WO | WO 02/092142 A3 | 11/2002 |
| WO | WO 2004/014969 | 2/2004 |
| WO | WO 2004/015090 | 2/2004 |
| WO | WO 2004/024035 | 3/2004 |
| WO | WO 2004/028356 | 4/2004 |
| WO | WO 2004/052254 | 6/2004 |
| WO | WO 2005/030102 | 4/2005 |
| WO | WO 2005/042043 | 5/2005 |

OTHER PUBLICATIONS

Han et al., "A fibrin-based bioengineered ocular surface with human corneal epithelial stem cells", Cornea, vol. 21 No. 5 2002, p. 505-510.
Miyajima, Hiroko., "At issue: the next generation of microkeratomes", Ocular Surgery news Europe/Asia-Pacific edition, Feb. 2002 5pgs.
Ophthalmology Times, "New LASIK device: CIBA vision to market subepithelial seperator", Aug. 1, 2002.
Online article, CIBA Vision website, "research and development" "Sub-epithelial Seperator", (2003).
Burrill, Alicia., "Gel-Assisted Lasek", Cataract & Refractive Surgery Today, (2003).
Nader, Nicole. "Learning a new language: understanding the terminology of wavefront-guided ablation", Ocular Surgery News, Feb. 1$^{st}$ 2003, found on OSN Supersite, 5 pgs.
"Licensing agreement for automated microkeratome-based device" found online at: http://www.optical-world.co.uk/Aug%202002%20international_outlook.htm, no author given, printed on Sep. 13, 2002.
Shimmura et al. "Collagen-Poly (N-Isopropylacrylamide)-Based Membranes for Corneal Stoma Scaffolds", Cornea vol. 22(Suppl. 1):S81-8, (2003).
Shimmural et al. "Biocompatibility of Collagen-Based Blended Biomaterials" Invest Ophthalmol Vis Sci 2002;43: E-Abstract 2997 (c) 2002 ARVO.
Jeong et al., "Thermosensitive sol-gel reversible hydrogels" Adv. Drug Deliv. Rev., 54:37-51 (2002).
Vernon et al., "Thermally Reversible Polymer Gels for Biohybrid Artificial Pancreas" Macromol. Symp., 109:155-167 (1996).
Stile et al., "Synthesis and Characterization of Injectable Poly(N-isopropylacrylamide)-Based Hydrogels That Support Tissue Formation in Vitro" Macromolecules, 32:7370-9 (1999).
Stile et al., "Poly(N-isopropylacrylamide)-Based Semi-interpenetrating Polymer Networks for Tissue Engineering Applications. 1. Effects of Linear Poly(acrylic acid) Chains on Phase Behaviour" Biomacromolecules 3:591-600 (2002).
Stile et al., "Thermo-Responsive Peptide-Modified Hydrogels for Tissue Regeneration" Biomacromolecules 2:185-194 (2001).
Hicks et al., "Keratoprostheses: Advancing Toward a True Artificial Cornea" Surv. Ophthalmol. 42:175-189 (1997).
Trinkaus-Randall and Nugent, "Biological Response to a Synthetic Cornea" Controlled Release 53:205-214, (1998).
Gutowska et al., "Thermosensitive Interpenetrating Polymer Networks: Synthesis, Characterization, and Macromolecular Release" Macromolecules, 27:4167-4175 (1994).
Yoshida et al., "Comb-type Grafted Hydrogels with Rapid De-Swelling Response to Temperature Changes" Nature, 374:240-242 (1995).
Lynn & Langer, "Degradable Poly(β-amino esters): Synthesis, Characterization, and Self-Assembly with Plasmid DNA" J. Amer. Chem. Soc., 122:10761-10768 (2000).
Ahmed et al., "Characterization and inhibition of fibrin hydrogel-degrading enzymes during development of tissue engineering scaffolds," Tissue Eng. 2007 Jul;13(7):1469-77.
Biowski et al., "Corneal Lathing Using the Excimer Laser and a Computer-controlled Positioning System," J Refract Surg. 2000 Jan.-Feb.;16(1):23-31.
Blais et al., "LBP and CD14 secreted in tears by the lacrimal glands modulate the LPS response of corneal epithelial cells," Invest Ophthalmol Vis Sci. Nov. 2005;46(11):4235-44.
Bloomfield et al., "The use of Eastman 910 monomer as an adhesive in ocular surgery. I. Biologic effects on ocular tissues," Am J Ophthalmol. Apr. 1963;55:742-748.

Bonatti et al., "A fibrin-related line of research and theoretical possibilities for the use of fibrin glue as a temporary basal membrane in non-perforated corneal ulcers and in photorefractive keratectomy (PRK)-operated corneas," Arq Bras Oftalmol. Sep.-Oct. 2007;70(5):884-889.

Bourne, "Clinical estimation of corneal endothelial pump function," Trans Am Ophthalmol Soc. 1998; 96: 229-242.

Carlsson et al., "Bioengineered corneas: how close are we?" Curr Opin Ophthalmol. Aug. 2003;14(4):192-197.

Controlled Release Society Newsletter, 2005; 22(2): 1-36.

Cox, "Correcting Ocular Wavefront Aberrations using Contact Lenses", University of Bradford, downloaded from the Internet:<<http://www.brad.ac.uk/acad/lifesci/optometry/index.php/Projects/CorrectingOcularWavefrontAberrationsUsingContactLenses>>, Last modified Oct. 7, 2003.

Delustro et al., "A comparative study of the biologic and immunologic response to medical devices derived from dermal collagen," J Biomed Mater Res. Jan. 1986;20(1):109-120.

Dohlman et al., "Further experience with glued-on contact lens (artificial epithelium)," Arch Ophthalmol. Jan. 1970;83(1):10-20.

Dohlman et al., "Replacement of the corneal epithelium with a contact lens (artificial epithelium)," Trans Am Acad Ophthalmol Otolaryngol. May-Jun. 1969;73(3):482-493.

Doillon et al., "A collagen-based scaffold for a tissue engineered human cornea: physical and physiological properties," Int J Artif Organs. Aug. 2003;26(8):764-773.

Dravida et al., "A biomimetic scaffold for culturing limbal stem cells: a promising alternative for clinical transplantation," J Tissue Eng Regen Med. Jul. 2008;2(5):263-271.

Duan etal, "Biofunctionalization of collagen for improved biological response: scaffolds for corneal tissue engineering," Biomaterials. Jan. 2007;28(1): 78-88.

Engel et al., "Repair of a Traumatic Scleral Rupture With Scleral Imbrication and BioGlue," Retina. Apr.-May 2007;27(4):505-8.

Epifix [Brochure], Surgical Biologics, downloaded from the Internet: http://http://www.surgicalbio.com/pdf/surgical_biologics_epifix_brochure.pdf>>, 2 pages total, (2009).

Evans et al. "Epithelialization of a Synthetic Polymer in the Feline Cornea: a Preliminary Study," Invest. Ophthalmol. Vis. Sci. 2000, 41(7):1674-1680.

Evans et al., "A review of the development of a synthetic corneal onlay for refractive correction," Biomaterials. Dec. 2001;22(24):3319-3328.

Evans et al., "Progress in the development of a synthetic corneal onlay," Invest. Ophthalmol. Vis. Sci. 2002; 43(10): 3196-3201.

Griffith et al., "Artificial human corneas: Scaffolds for transplantation and host regeneration" Cornea. Oct. 2002;21(7 Suppl): S54-61.

Griffith et al., "Functional Human Corneal Equivalents Constructed from Cell Lines," Science Dec. 10, 1999, 286(5447):2169-2172.

Homolka et al., "Laser shaping of corneal transplants in vitro: area ablation with small overlapping laser spots produced by a pulsed scanning laser beam using an optimizing ablation algorithm," Phys. Med. Biol. 1999, 44:1169-1180.

Ibrahim-Elzembely, "Human fibrin tissue glue for corneal lamellar adhesion in rabbits: a preliminary study.," Cornea. Nov. 2003;22(8):735-739.

Jones et al., "Silicone Hydrogel Contact Lens Materials Update—Part 1", downloaded from the Internet: <<http://www.siliconehydrogels.com/editorials/index_july.asp>>, Jul. 2004, 4 pages total.

Jones et al., "Silicone Hydrogel Contact Lens Materials Update—Part 2", downloaded from the Internet: <<http://www.siliconehydrogels.com/editorials/index_august.asp>>, Aug. 2004, 4 pages total.

Kaminski et al., "Ten-year follow-up of epikeratophakia for the correction of high myopia," Ophthalmology. Nov. 2003;110(11):2147-2152.

Kaufman et al., "Human fibrin tissue adhesive for sutureless lamellar keratoplasty and scleral patch adhesion a pilot study," Ophthalmology, 110(11): 2168-2172, (2003).

Khadem et al., "Healing of perforating rat corneal incisions closed with photodynamic laser-activated tissue glue," Lasers in surgery and medicine 2004;35(4):304-311.

Klenkler et al., "EGF-grafted PDMS surfaces in artificial cornea," Biomaterials. Dec. 2005;26(35):7286-96.

Lagali et al., "Innervation of tissue-engineered corneal implants in a porcine model: a 1-year in vivo confocal microscopy study," Invest Ophthalmol Vis Sci. Aug. 2007;48(8): 3537-3544.

Lagali et al., "Innervation of tissue-engineered recombinant human collagen-based corneal substitutes: a comparative in vivo confocal microscopy study," Invest Ophthalmol Vis Sci. Sep. 2008;49(9): 3895-902.

Latkany et al., "Plasma surface modification of artificial corneas for optimal epithelialization," J. Biomed Mater Res 1997; 36(1):29-37.

Lekskul et al., "CxGELSIX: a novel preparation of type VI collagen with possible use as a biomaterial," rnea. Mar. 2000;19(2):194-203.

Li et al., "Cellular and nerve regeneration within a biosynthetic extracellular matrix for corneal transplantation," Proc Natl Acad Sci U S A. Dec. 23, 2003;100(26): 15346-15351.

Li et al., "Recruitment of multiple cell lines by collagen-synthetic copolymer matrices in corneal regeneration," Biomaterials. Jun. 2005;26(16):3093-3104.

Liu et al., "A simple, cross-linked collagen tissue substitute for corneal implantation," Invest Ophthalmol Vis Sci. May 2006;47(5): 1869-1875.

Liu et al., "Alginate microsphere-collagen composite hydrogel for ocular drug delivery and implantation," J Mater Sci Mater Med. Nov. 2008;19(11): 3365-3371.

Liu et al., "Immunological responses in mice to full-thickness corneal grafts engineered from porcine collagen," Biomaterials Sep. 2007;28(26): 3807-3814.

Liu et al., "Properties of porcine and recombinant human collagen matrices for optically clear tissue engineering applications," Biomacromolecules. Jun. 2006;7(6):1819-1828.

Liu et al., "Recombinant human collagen for tissue engineered corneal substitutes," Biomaterials. Mar. 2008;29(9): 1147-1158.

Matteini et al., "Microscopic characterization of collagen modifications induced by low-temperature diode-laser welding of corneal tissue," Lasers in surgery and medicine 2007;39(7):597-604.

Maury et al., "In-vitro development of corneal epithelial cells on a new hydrogel for epikeratoplasty," J Mater Sci Mater Med. Sep. 1997;8(9):571-576.

McDonald, "The future direction of refractive surgery," J Refract Surg 1988; 4(5):158-168.

McLaughlin et al., "Regeneration of corneal cells and nerves in an implanted collagen corneal substitute," Cornea. Jun. 2008;27(5): 580-589.

Menabuoni et al., "Laser-assisted corneal welding in cataract surgery: Retrospective study," J Cataract Refract Surg. Sep. 2007;33(9):1608-1612.

Merrett et al., "Tissue-engineered recombinant human collagen-based corneal substitutes for implantation: performance of type I versus type III collagen," Invest Ophthalmol Vis Sci. Sep. 2008;49(9): 3887-3894.

Moore et al., "Fate of lyophilized xenogeneic corneal lenticules in intrastromal implantation and epikeratophakia," Invest Ophthalmol Vis Sci. Mar. 1987;28(3):555-559.

Nakamura, "Histopathological and immunohistochemical studies of lenticules after epikeratoplasty for keratoconus," British Journal of Ophthalmology 2005;89:841-846.

Pierce Crosslinking Reagents Technical HandBook, pp. 16-23. downloaded from the Internet:<<http://www.piercenet.com/files/1601361Crosslink.pdf.>>, (2006).

Rafat et al., "PEG-stabilized carbodiimide crosslinked collagen-chitosan hydrogels for corneal tissue engineering," Biomaterials. Oct. 2008;29(29): 3960-3972.

Rafat et al., "Surface modification of collagen-based artificial cornea for reduced endothelialization" J Biomed Mater Res A. Mar. 20, 2008. [Epub ahead of print].

Richards et al., "The relation of the corneal surface to the permanence of glued-on contact lenses," Can J Ophthalmol. Apr. 1971;6(2):98-103.

Ruben "Adhesive keratoprostheses," Trans Ophthalmol Soc U K. 1970;90:551-564.

Schmitz, 'Excimer laser "corneal shaping": a new technique for customized trephination in penetrating keratoplasty,' Graefe's Archive for Clinical and Experimental Ophthalmology, May 2003; 241:423-431.

Stenzel et al., "Collagen as a biomaterial," Annu. Rev. Biophys. Bioeng. 1974; 3:231-253.

Suuronen et al., "Functional innervation in tissue engineered models for in vitro study and testing purposes," Toxicol Sci. Dec. 2004;82(2):525-533.

Suuronen et al., "Innervated human corneal equivalents as in vitro models for nerve-target cell interactions," The FASEB Journal. 2004;18:170-172.

Suuronen et al., "Tissue-engineered injectable collagen-based matrices for improved cell delivery and vascularization of ischemic tissue using CD133+ progenitors expanded from the peripheral blood," Circulation. Jul. 4, 2006;114(1 Suppl):I138-44.

Sweeney et al., "A synthetic polymer as a corneal onlay ," [ARVO Abstract] Invest Ophthalmol Vis Sci 40(4),S638Abstract nr 3361, (1999).

Trinkaus-Randall et al. "Implantation of a synthetic cornea: design, development and biological response," Artif Organs. Nov. 1997;21(11):1185-1191.

Vascotto et al., "Localization of candidate stem and progenitor cell markers within the human cornea, limbus, and bulbar conjunctiva in vivo and in cell culture," Anat Rec A Discov Mol Cell Evol Biol. Aug. 2006;288(8):921-931.

Vinciguerra et al., "Butterfly laser epithelial keratomileusis for myopia," Journal of refractive surgery 2002;18(3 Suppl):S371-3.

U.S. Appl. No. 60/715,411, filed Sep. 9, 2005.

US 6,773,442, 08/2004, Pallikaris et al. (withdrawn)

* cited by examiner

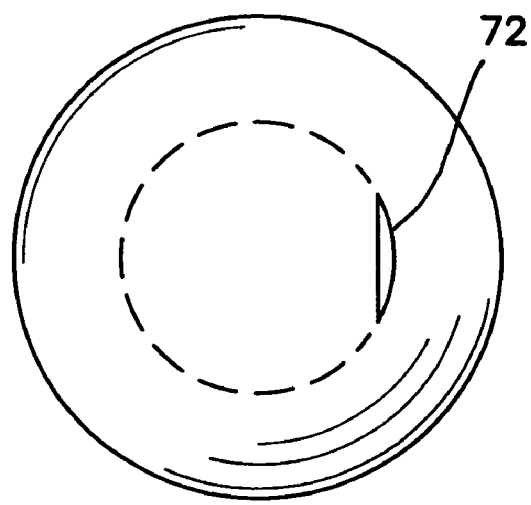
FIG. 11A
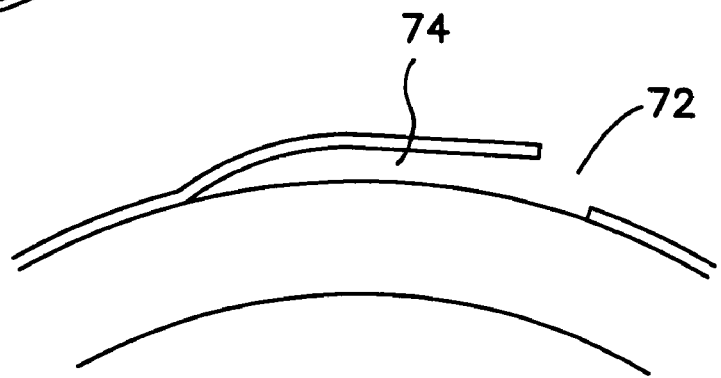
FIG. 11B
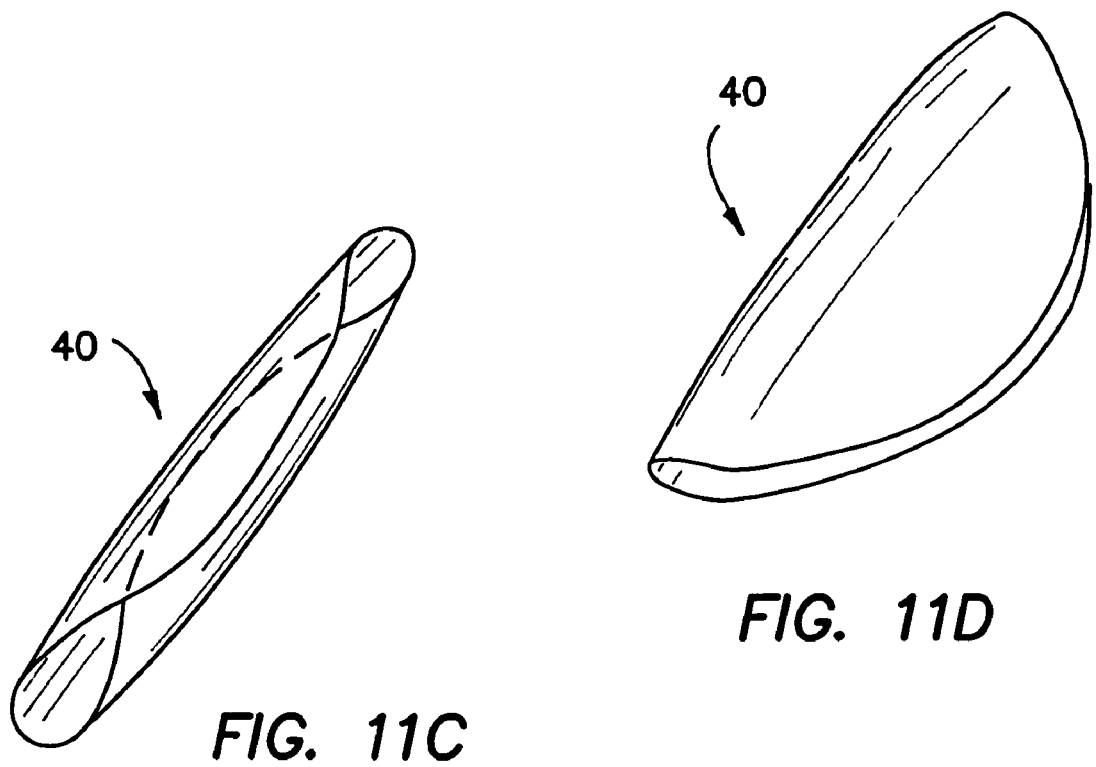
FIG. 11C
FIG. 11D

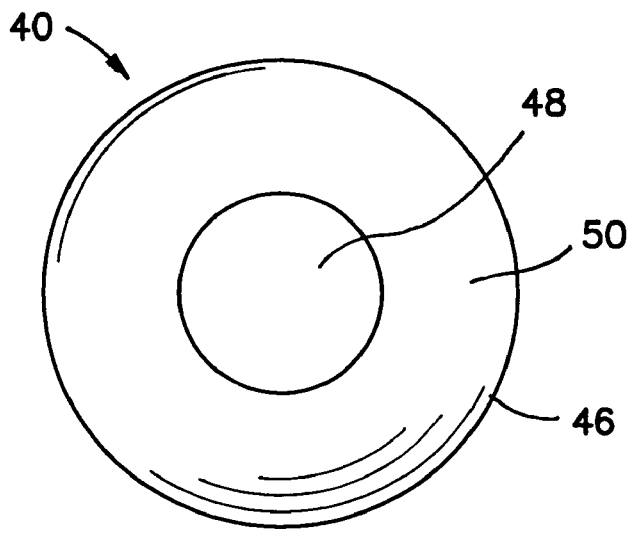
FIG. 12A
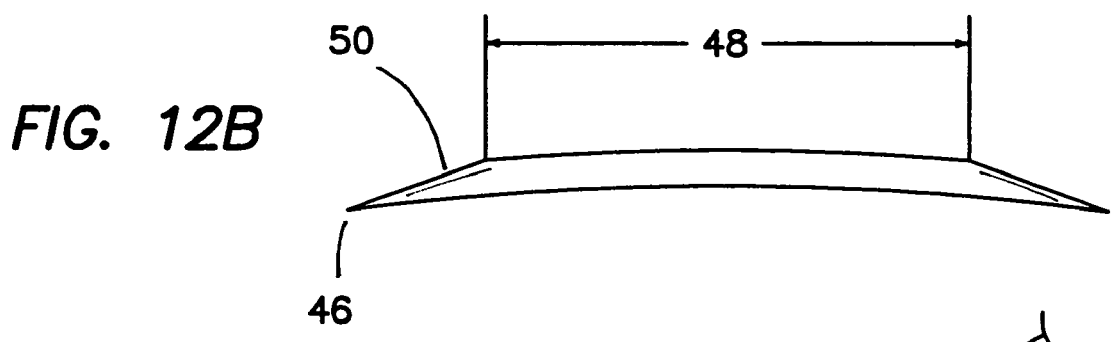
FIG. 12B
FIG. 12C
FIG. 12E
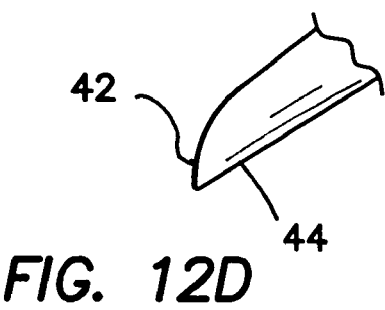
FIG. 12D

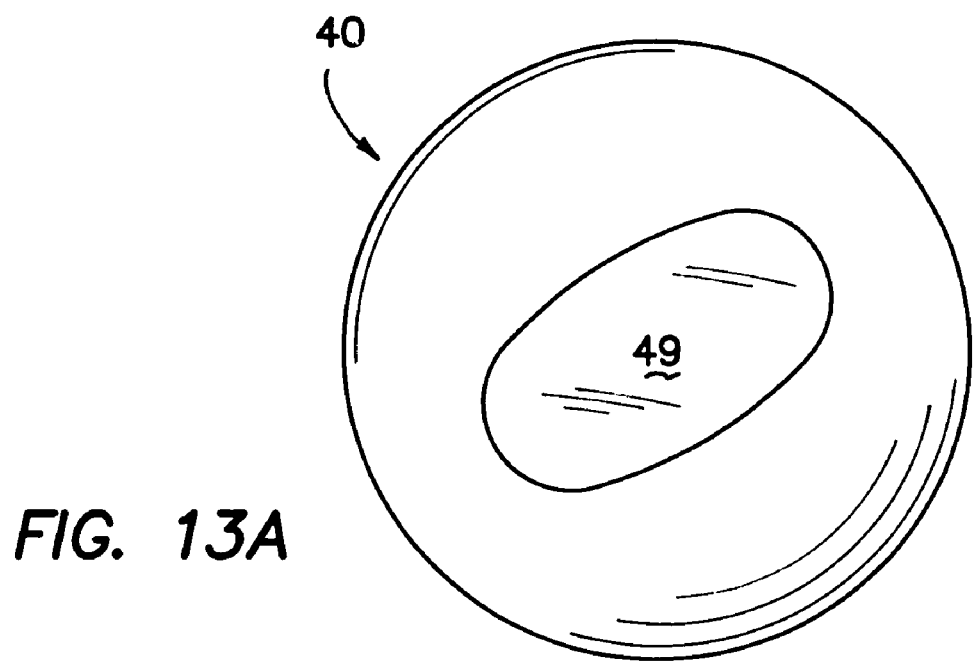
FIG. 13A
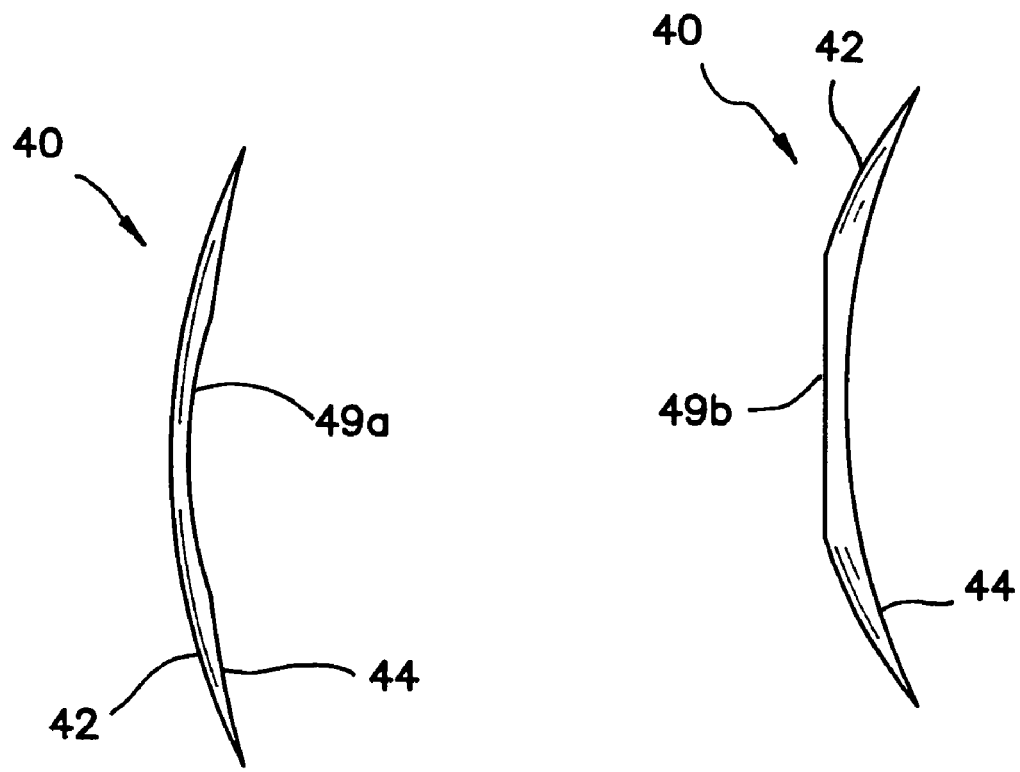
FIG. 13B
FIG. 13C

US 7,828,844 B2

INSERTING LENSES INTO CORNEAL EPITHELIAL POCKETS TO IMPROVE VISION

CROSS-REFERENCE TO RELATED APPLICATIONS

This application claims the benefit of U.S. Provisional Application No. 60/464,590, filed Apr. 21, 2003, and U.S. Provisional Application No. 60/464,004, filed Apr. 18, 2003, and U.S. Provisional Application No. 60/410,837, filed Sep. 13, 2002, the disclosures of all of which are hereby incorporated by reference.

BACKGROUND OF THE INVENTION

1. Field of the Invention

The present invention relates to devices and methods of improving a patient's vision. In particular, the invention relates to improving vision of a patient by placing a corrective ocular device between an epithelium of the patient's eye and the stroma of the cornea of the patient's eye. The corrective ocular device may be a lens, including a corneal onlay. The corrective ocular device may have a preformed epithelial cell layer secured over the device when placed on an eye of a patient. The preformed epithelial cell layer may be synthesized in vitro or the preformed epithelial cell layer may include at least a portion of the patient's corneal epithelium.

2. Description of Related Art

The cornea of the human eye provides between approximately 60 and 70 percent of the focusing power of the eye. As understood in the art, lenses may be placed in proximity of the cornea to augment the focusing capabilities of the eye. Examples of vision correction lenses include corneal inlays, which are implanted within the cornea, corneal onlays, which are placed over the cornea after the epithelium has been removed, and contact lenses, which are placed over the corneal epithelium. Corneal onlays differ from contact lenses in that corneal onlays are covered by an epithelial cell layer compared to contact lenses that are placed over the corneal epithelium.

Because corneal onlays are placed on a deepithelialized cornea, it is necessary for the epithelium to be replaced over the onlay to prevent damage and infection to the eye. Epithelial cells develop from the corneal limbus and migrate over the eye. Unfortunately, many materials from which existing corneal onlays are manufactured from do not effectively promote epithelial cell growth and migration over the onlay.

Some attempts have been made to create corneal onlays that attempt to improve the migration of epithelial cells over the onlay. For example, U.S. Pat. No. 5,171,318 discloses the use of fibronectin disposed over the surface of an onlay to facilitate cell migration over the onlay and attachment to the onlay. U.S. Pat. No. 5,713,957 discloses non-biodegradable non-hydrogel corneal onlays having large pores in the periphery of the onlay, which are intended to facilitate securement of the onlay to the eye by permitting cells to grow through the pores. U.S. Pat. No. 5,836,313 discloses a composite hydrogel corneal onlay that comprises a layer of corneal tissue or collagen to improve cell migration over the corneal onlay. U.S. Pat. No. 5,994,133 discloses corneal onlays fabricated from various polymers that permit epithelial cells to migrate over the onlay. U.S. Patent Publication No. US 2001/0047203 A1 discloses corneal onlays with surface indentations that supports attachment and migration of the epithelial cells over the onlay. PCT Publication No. WO 02/06883 discloses a corneal onlay derived from donor corneal tissue. In addition, WO 02/06883 appears to disclose the use of an epithelial cell layer placed over the onlay; the epithelial cell layer may be obtained from donor tissue, such as fetal or embryonic tissue, or autologous tissue biopsies of corneal epithelial cells. The corneal onlays which require epithelial cells to migrate over the onlay surface fail to provide satisfactory coverage of the onlay with the epithelium. For example, when epithelial cells are required to migrate over corneal onlays, the epithelial cells may not differentiate fully. Moreover, as the epithelial cells migrate, there may be a tendency for the epithelium to grow under the corneal onlay placed over the eye and cause the onlay to be dislodged or encapsulated. In addition, the recovery time for the epithelial cells to grow and migrate over the onlay is prohibitive and contributes to the undesirability of these approaches.

While WO 02/06883 discloses the use of cultured epithelial cells to create a layer of epithelium that may be used to cover a corneal onlay, it does not disclose using cultured stem cells to create a layer of epithelium. Indeed, culturing stem cells to create a corneal epithelium has only recently been explored (e.g., see Han et al., "A fibrin-based bioengineered ocular surface with human corneal epithelial stem cells", *Cornea*, 21(5): 505-510 (2002); and U.S. Patent Publication No. US 2002/0039788 A1). These references disclose culturing corneal epithelial stem cells to repair damaged ocular surfaces. Although complications did not appear to be too significant for correcting damaged ocular surfaces, it was noted that it may be problematic to use cultured stem cells with corrective lenses.

SUMMARY OF THE INVENTION

The present invention is directed to a corneal appliance or ocular device that is structured to improve a patient's vision, and methods of improving or correcting a patient's vision. The corneal appliance has a lens or a lenticule, and a layer of epithelial cells disposed over the lens.

In one aspect, the epithelial cells may be derived from autologous stem cells, or in other words, from stem cells obtained from the patient receiving the corneal appliance.

In another aspect, the epithelial cells may include at least a portion of the patient's corneal epithelium that has been separated from Bowman's membrane and/or the stroma of the patient's cornea.

A corneal appliance has been invented that addresses the problems associated with current corneal onlays, and the use of epithelial cells in conjunction with onlays. In addition, methods of correcting a patient's vision have been invented that include inserting a corrective ocular device beneath the corneal epithelium of the patient.

A corneal appliance that is structured to be placed over a deepithelialized eye includes a lens and a layer of epithelial cells fixedly positioned over the lens. The epithelial cells of the appliance may be derived from stem cells, which are grown in culture, or may be epithelial cells of the patient receiving the corneal appliance. The stem cells used may include corneal limbal stem cells, or may be exclusively corneal limbal stem cells.

A corneal appliance, as disclosed herein, may be manufactured by a process comprising steps of culturing stem cells until at least a fraction of the stem cells have differentiated into corneal epithelial cells; and applying a plurality of cells obtained from the culture over an anterior surface of a lens to form a layer of epithelial cells that are fixedly secured over the lens before the lens is placed on an eye.

In addition, a corneal appliance may be obtained by a process of inserting a lens underneath an epithelium of an eye substantially without exposing or uncovering the underlying corneal surface and allowing the epithelium to be fixedly secured over the lens.

The lens of the corneal appliance may include collagen, including recombinant collagen. The lens may be a synthetic stroma having a desired optical power, or the lens may be made from a hydrogel or non-hydrogel material suitable for vision correction lenses. The lens may be structured to facilitate attachment of the cells to the lens, for example, by creating indentations in the lens. Alternatively, or in addition, the appliance may include a cellular attachment element disposed between the lens and the epithelial cells.

The cells of the appliance may be derived from cultured stem cells that are grown in vivo or ex vivo. For example, the cells may be cultured in a culture dish, and then transferred to the lens. The cells may be transferred in a suspension, or as a layer of cells. The cells may be cultured on a surface of the lens. For example, the cells may be cultured on a lens positioned in a lens mold adapted to provide conditions suitable for culturing cells. Or, the cells may be cultured on the lens when the lens is placed over an eye. The cells that are applied to the lens may be stem cells, a mixture of stem cells and differentiated epithelial cells, or differentiated epithelial cells without stem cells.

The epithelial cells of the corneal appliance may also be part of a layer of corneal epithelium of the patient receiving the appliance. For example, a layer or flap of epithelium of the patient may be created by separating the epithelium from the cornea of the patient. The layer may be completely removed from the cornea, or may be partially removed to create a flap that remains attached to the remaining epithelium of the patient. The layer or flap of epithelial cells may then be placed over the lens body of the corneal appliance. In one embodiment, the layer of epithelial cells is encouraged to attach to the lens body by providing a suspension of stem cells over the lens body. In addition, the epithelial cells may be a part of the epithelium that is separated from Bowman's membrane, but that is not part of an epithelial flap. For example, the epithelial cells may be a portion of an epithelial pocket, such as, a portion of a preformed layer of epithelium that is located in proximity to where the layer of the epithelium begins to separate from the Bowman's membrane or stroma of the eye.

Any feature or combination of features described herein are included within the scope of the present invention provided that the features included in any such combination are not mutually inconsistent as will be apparent from the context, this specification, and the knowledge of one of ordinary skill in the art. In addition, any feature or combination of features may be specifically excluded from any embodiment of the present invention.

Additional advantages and aspects of the present invention are apparent in the following detailed description.

BRIEF DESCRIPTION OF THE FIGURES

FIG. 11A is an illustration of a front plan view of an eye having an offset epithelial incision.

FIG. 11B is a sectional view of the eye of FIG. 11A.

FIG. 11C is an illustration of a perspective view of a folded lens configured to be inserted in an epithelial incision.

FIG. 11D is an illustration of a perspective view of a folded lens in which the lens is folded along its midline.

FIG. 12A is an illustration of a front plan view of a corneal onlay lens.

FIG. 12B is a sectional view of the lens of FIG. 12A.

FIG. 12C is a magnified sectional view of an edge of an onlay lens in which the edge is rounded.

FIG. 12D is a magnified sectional view of an edge of an onlay lens in which the edge includes a rounded anterior portion, and an apex on the posterior portion.

FIG. 12E is a magnified sectional view of an edge of an onlay lens in which the edge is similar to a knife edge.

FIG. 13A is an illustration of a front plan view of an onlay lens structured to correct an astigmatism.

FIG. 13B is a sectional view of an onlay lens similar to FIG. 13A in which the posterior surface of the lens includes a torus.

FIG. 13C is a sectional view of an onlay lens similar to FIG. 13A in which the anterior surface of the lens includes a torus.

DETAILED DESCRIPTION

Figure 1:
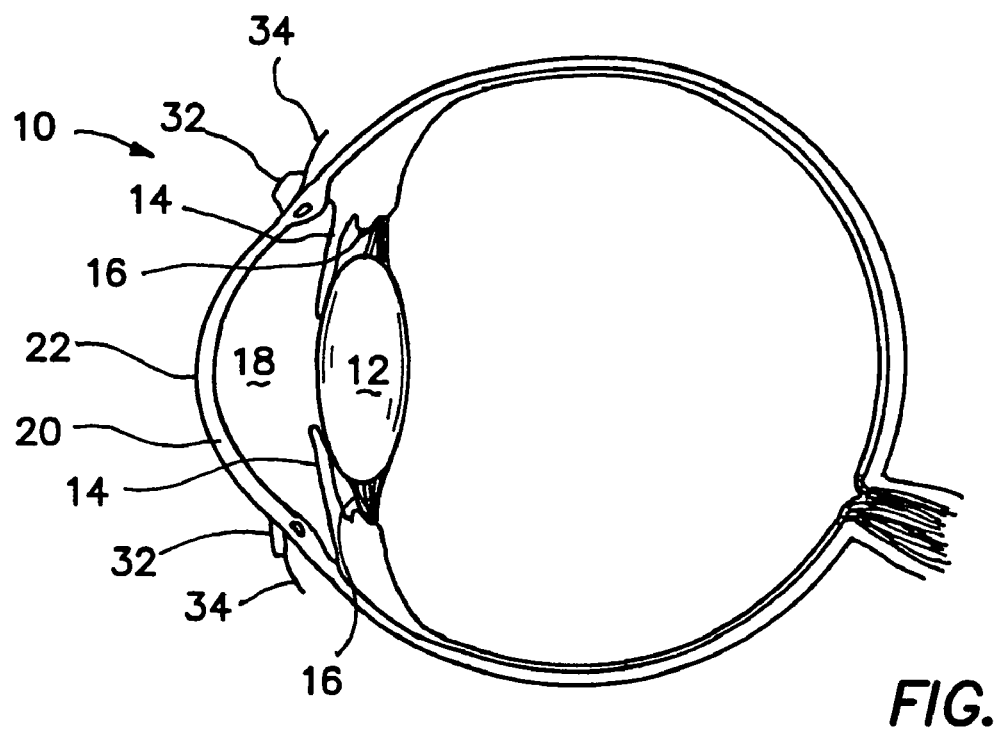
FIG. 1 is a diagram of a sectional view of a human eye.

As illustrated in FIG. 1, a typical human eye 10 has a lens 12 and an iris 14. Posterior chamber 16 is located posterior to iris 14 and anterior chamber 18 is located anterior to iris 14. Eye 10 has a cornea 20 that consists of five layers, as discussed herein. One of the layers, corneal epithelium 22, lines the anterior exterior surface of cornea 20. Corneal epithelium 22 is a stratified squamous epithelium that extends laterally to the limbus 32. At limbus 32, corneal epithelium 22 becomes thicker and less regular to define the conjunctiva 34.

Figure 2:
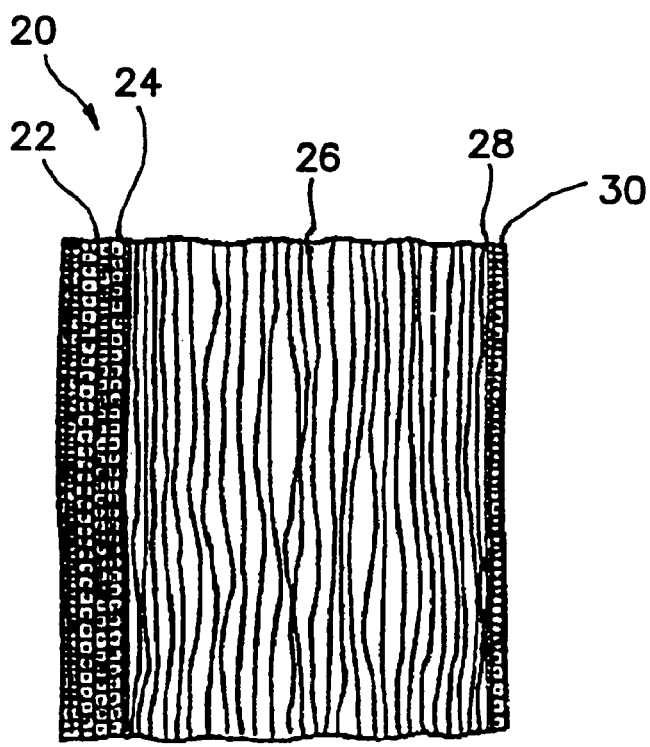
FIG. 2 is a diagram of a magnified sectional view of the cornea of the human eye of FIG. 1.

FIG. 2 illustrates a magnified view of the five layers of cornea 20. Typically, cornea 20 comprises corneal epithelium 22, Bowman's membrane 24, stroma 26, Descemet's membrane 28, and endothelium 30. Corneal epithelium 22 usually is about 5-6 cell layers thick (approximately 50 micrometers thick), and generally regenerates when the cornea is injured. Corneal epithelium 22 provides a relatively smooth refractive surface and helps prevent infection of the eye. Bowman's membrane 24 lies between epithelium 22 and the stroma 26 and is believed to protect the cornea from injury. Corneal stroma 26 is a laminated structure of collagen which contains cells, such as fibroblasts and keratocytes, dispersed therein. Stroma 26 constitutes about 90% of the corneal thickness. Corneal endothelium 30 typically is a monolayer of low cuboidal or squamous cells that dehydrates the cornea by removing water from the cornea. An adult human cornea is typically about 500 µm (0.5 mm) thick and is typically devoid of blood vessels.

Limbus 32, shown in FIG. 1, is a region of transitions where cornea becomes sclera, and conjunctiva. Limbus 32 contains stem cells, which are capable of differentiating into corneal epithelial cells, as described herein.

Figure 3A:
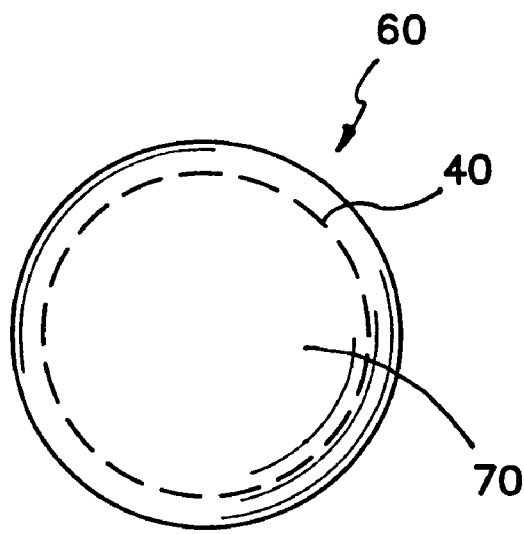
FIG. 3A is a diagram of a front plan view of a corneal appliance, as described herein.
Figure 3B:
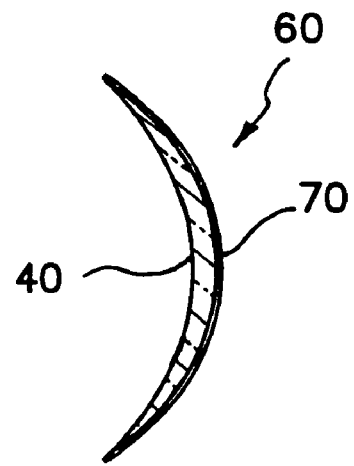
FIG. 3B is a sectional view of the corneal appliance of FIG. 3A.

A corneal appliance 60 has been invented, as illustrated in FIG. 3A, that is structured to be placed over a deepithelialized eye and that generally comprises a lens 40 and a layer of epithelium 70, or a layer of epithelial cells, located over the lens. Corneal appliance 60 is structured to alter the focusing capabilities of a patient's eye, and preferably, the corneal appliance is structured to improve vision of a patient. Corneal appliance 60 is intended to be placed over a deepithelialized cornea of an eye, and accordingly, corneal appliance 60 may be a corneal onlay. Corneal appliance 60 includes a layer of epithelium 70 which reduces the healing time of a patient required after surgery, as compared to corneal onlays which depend on the regeneration and migration of epithelial cells over the corneal onlay after it is placed over the eye. In addition, the preformed layer of epithelium 70 provides more uniform epithelial coverage over the cornea as compared to conventional corneal onlays.

As disclosed herein, the epithelial cells located over the lens may be obtained from the patient receiving the corneal appliance, and may be derived from stem cells of the patient, such as limbal stem cells, which may be cultured in vitro to define the layer of epithelium of the appliance. Autologous stem cells contribute to reduced immunogenicity experienced by the patient receiving the appliance as compared to corneal onlays that utilize non-autologous sources of epithelial cells, such as from embryonic or fetal tissue. In addition, use of patient-specific stem cells reduces the amount of biopsy tissue required for corneal onlays using mature or differentiated epithelial cells.

Alternatively, the layer of epithelial cells may be formed by detaching a portion of a patient's epithelium to create an epithelial flap that can be resected and then placed back over a corneal onlay after the onlay has been placed over the eye. The incision around the flap may be mended over the onlay, as discussed herein, to maintain the onlay in a desired position over the eye. The preformed layer of epithelial cells may also be a portion of the patient's corneal epithelium that has been separated from the underlying Bowman's membrane or corneal stroma. The preformed layer may be separated from the underlying corneal structures with or without making an epithelial flap, depending on the particular embodiment of the invention. For example, an incision may be made in the epithelium to provide access to the region between the epithelium and Bowman's membrane. The epithelium can be separated from Bowman's membrane by introducing a separator through the incision. The separator may be a surgical device or may include a substance that can be injected through the incision. The separator effectively separates the epithelium from Bowman's membrane without significantly damaging Bowman's membrane. However, the separator may also enable a relatively small cut to be made in Bowman's membrane, without substantially damaging Bowman's membrane, which may facilitate placement of the lens over the stroma and may promote more rapid and satisfactory healing of the eye. The corrective ocular device, such as a corneal onlay, may then be inserted between the epithelium and Bowman's membrane. Advantageously, in this embodiment, the epithelium is not required to be realigned after insertion of the ocular device, and misalignment problems of the ocular device are reduced. Among other things, the lens 40 is maintained in a substantially fixed position on an eye relative to a lens, for example, a substantially identical lens, that is placed on an eye so that the epithelium is required to regenerate and migrate over the lens.

Figure 4A:
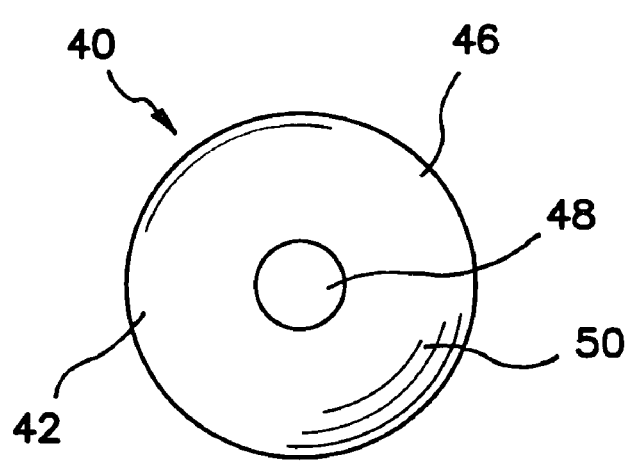
FIG. 4A is a diagram of a front plan view of a lens used in a corneal appliance, as described herein.
Figure 4B:
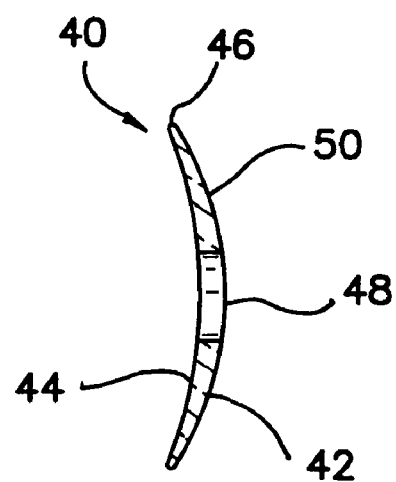
FIG. 4B is a sectional view of the lens of FIG. 4A.

The lens 40 used in corneal appliance 60 may be fabricated from any suitable material that is optically clear to permit light to be transmitted to the retina of the eye when corneal appliance 60 is placed over the eye without compromising the ocular physiology of the eye. Lens 40 has an anterior surface 42, a posterior surface 44, a peripheral edge 46 disposed at the juncture of anterior surface 42 and posterior surface 44, as illustrated in FIGS. 4A and 4B. Anterior surface 42 is typically convex and posterior surface 44 is typically concave, however, the posterior surface may also include one or more planar portions or surfaces, or may be substantially planar. Lens 40 may also include an optic zone 48 and a peripheral zone 50. Typically, optic zone 48 is bounded by peripheral zone 50, or in other words, optic zone is generally centrally located about an optical axis, such as a central optical axis, of the lens and peripheral zone 50 is disposed between an edge of optic zone 48 and peripheral edge 46. Additional zones and lens configurations may be provided with the lens depending on the particular visual deficiency experienced by the patient. In addition, the lenses may have junctionless zones, such as two or more zones that do not have a visually or optically detectable junction. The zones of the lenses may be smooth and continuous, and the lenses may be optically optimized to correct not only refractive errors, but also other optic aberrations of the eye and/or the optical device independently or in combination with correcting refractive errors. As understood by persons skilled in the art, lens 40 may be structured to correct visual deficiencies including, and not limited to, myopia, hyperopia, astigmatism, and presbyopia. The lens may correct or improve visual deficiencies by either optical means or physical means imposed on the stroma of the eye, or a combination thereof. Thus, the lens 40 of corneal appliance 60 may be a monofocal lens or a multifocal lens, including, without limitation, a bifocal lens. In addition, or alternatively, the lens 40 may be a toric lens, such as the lens illustrated in FIGS. 13A, 13B, and 13C. For example, the lens 40 may include a toric region 49 which may be effective when placed on an eye with an astigmatism to correct or reduce the effects of the astigmatism. The lens 40 may include a toric region 49*a* located on the posterior surface 44 of the lens 40, as shown in FIG. 13B, or the lens 40 may include a toric region 49B located on the anterior surface 42, as shown in FIG. 13C. Advantageously, toric lenses may be used without requiring a ballast to maintain proper orientation of the lens on the eye since the lens may be held in a relatively fixed position by the epithelium of the appliance. However, a ballast may be provided if desired. In certain embodiments, the lens 40 may include a ballast, such as a prism, or it may include one or more thinned regions, such as one or more inferior and/or superior thin zones. In lenses configured to correct presbyobia, the lens may include one or more designs, such as concentric, aspheric (either with positive and/or negative spherical aberration), diffractive, and/or multi-zone refractive.

In certain embodiments of the corneal appliance 60, the lens may have an optical power ranging from about −10.00 diopters to about +10.00 diopters, although other optical powers may be provided, and such other optical powers are within the scope of the present invention. Typically, a lens of the corneal appliance will have a diameter between about 6 mm and about 12 mm. Preferably, the diameter of the lens will be between about 7 mm and about 10 mm. The optic zone of the lens typically ranges from about 5 to about 11 mm, and preferably ranges from about 6 mm to about 8 mm, in diameter. The optic zone may be provided on either the anterior or posterior surface of the lens.

The posterior surface of the lens 40 is specifically configured to substantially align with the anterior surface of a deepithelialized eye. Thus, the posterior surface of the lens 40 may include one or more spherical or aspherical dimensions with a base curve that ranges from about 5.0 mm to about 12.0 mm in diameter, preferably from about 6.0 mm to about 9.0 mm, and more preferably about 7.0 mm to about 8.5 mm. The thickness of the lens 40 at or near the center of the lens (i.e., the center thickness) is typically greater than about 10 micrometers and is less than about 300 micrometers. Preferably, the center thickness is between about 30 micrometers and about 200 micrometers. The exact or specific thickness of the central region may be determined on a case-by-case basis by one of ordinary skill in the art since the maximum thickness is optical power and refractive index dependent.

The thickness of the peripheral edge 46 of the lens 40 is typically, but not always, less than the center thickness, as shown in FIGS. 12A, 12B, 12C, 12D, and 12E. The edge thickness should be thin enough to facilitate epithelial cell growth at the juncture of the lens and the Bowman's membrane or stroma of an eye, and may be thin enough to promote additional epithelial cell migration over the edge of the lens. Typically, the edge thickness of the lens is less than about 120 micrometers. In certain embodiments, the lens 40 has an edge thickness less than about 60 micrometers, and preferably less than about 30 micrometers. In a preferred embodiment, the lens 40 has an edge thickness of about 0 micrometers (for example, the thickness of a sharp knife edge). As shown in FIG. 12C, the lens edge may be rounded on both the anterior and posterior surfaces, as shown at 46A. Alternatively, the lens edge may include a rounded anterior surface 42 and an apex on or near the posterior surface 44, as shown at in FIG. 12D. Or, the lens edge may be shaped as a knife edge, such as at 46B as shown in FIG. 12E.

Lens 40 may comprise synthetic or non-synthetic materials, and combinations thereof. As used herein, the phrase synthetic materials refers to materials that are not obtained, for example, are not obtained directly, from animal subjects. Thus, synthetic materials specifically exclude donor corneal tissue.

In one embodiment, lens 40 may be made from collagen, such as purified collagen. The collagen may be collagen Type I, which is the type of collagen that defines the bulk of the corneal stroma, or lens 40 may be made from other types of collagen, including combinations of different types of collagen, such as types III, IV, V, and VII. In certain embodiments, the collagen may be obtained from animals, including humans. For example, collagen of the lens 40 may be bovine collagen, porcine collagen, avian collagen, murine collagen, equine collagen, among others. Many different types of collagen useful in the lenses of the present invention are publicly available from companies, such as Becton Dickenson. In other embodiments, the collagen may be recombinantly synthesized, such as by using recombinant DNA technology. Preferably, lens 40 is not obtained from a donor patient, such as from corneal tissue of another individual person. Collagen may be obtained using any conventional technique, as is practiced in the art. One source of publicly available recombinant collagen is FibroGen, South San Francisco, Calif. Alternatively, or in addition, recombinant collagen may be prepared and obtained using the methods disclosed in PCT Publication No. WO 93/07889 or WO 94/16570. The recombinant production techniques described in these PCT publications may readily be adapted so as to produce many different types of collagens, human or non-human. Utilizing purified collagen simplifies procedures of making corneal onlays, as compared to corneal onlays that are obtained from donor tissue, such as disclosed in PCT Publication No. WO 02/06883. For example, using purified collagen, including recombinantly synthesized collagen, steps of decellularization donor corneal tissue are avoided. Furthermore, the collagen may be fully biodegradable or partially biodegradable, which may facilitate attachment of epithelial cells over the onlay by permitting native collagen created by the patient receiving the onlay to integrate and/or replace the collagen of the corneal appliance. The collagen used to manufacture lens 40 may be populated with cells, such as corneal keratocytes, before being used in corneal appliance 60. Cells may be added to the collagen by culturing a suspension of keratocytes and subsequently immersing the lens in a keratocyte medium, as disclosed in WO 02/06883. It is preferable that the cells that are used to populate the lens do not generate an immune response, or generate a minimal immune response. Accordingly, the cells may be from an allogenic source, such as another person, an autologous source, such as the patient receiving the appliance, or may be from a xenogenic source. As understood by persons of ordinary skill in the art, cells obtained from xenogenic sources may need to be modified to reduce the antigenicity or immunogenicity of the cells when administered to the patient to reduce the likelihood of developing an immune response. Alternatively, in embodiments where the lens is placed over a Bowman's membrane that has one or more openings, keratocytes from the patient's own stroma may populate the collagen lens, and the integration between the lens and the stroma may facilitate the fixation of the lens on the eye.

Alternatively, lens 40 may be manufactured by obtaining and culturing corneal keratocytes, as disclosed in PCT Publication No. WO 99/37752 and U.S. Pat. No. 5,827,641. The cultures of keratocytes will be placed in a mold suitable for a vision correction lens, and will produce a collagen matrix similar to a normal stroma in vivo. The various molds will thus produce a corneal appliance having a synthetic stroma with a desired optical power to correct a vision deficiency of the patient.

Lens 40 of corneal appliance 60 may be made from a polymeric hydrogel, as understood by persons of ordinary skill in the art. A polymeric hydrogel includes a hydrogel-forming polymer, such as a water swellable polymer. The hydrogel itself includes such a polymer swollen with water.

Polymeric hydrogels useful as corneal appliance lenses, for example, corneal onlays, typically have about 30% to about 80% by weight water, but may have about 20% to about 90% by weight water, or about 5% to about 95% by weight water, and have refractive indices between about 1.3 and about 1.5, for example about 1.4, which is similar to the refractive indices of water and a human cornea.

Examples of suitable hydrogel-forming polymer materials or components of the disclosed lenses include, without limitation, poly(2-hydroxyethyl methacrylate) PHEMA, poly(g-lycerol methacrylate) PGMA, polyelectrolyte materials, polyethylene oxide, polyvinyl alcohol, polydioxaline, poly (acrylic acid), poly(acrylamide), poly(N-vinyl pyrilidone) and the like and mixtures thereof. Many of such materials are publicly available. In addition, one or more monomers which do not themselves produce homopolymers which are not hydrogel-forming polymers, such as methylmethacrylate (MMA), other methacrylates, acrylates and the like and mixtures thereof, can also be included in such hydrogel-forming polymer materials provided that the presence of units from such monomers does not interfere with the desired formation of a polymeric hydrogel.

Alternatively, and in certain embodiments, lens 40 of corneal appliance 60 may be manufactured from a biocompatible, non-hydrogel material or component, such as disclosed in U.S. Pat. No. 5,713,957. Examples of non-hydrogel materials include, and are not limited to, acrylics, polyolefins, fluoropolymers, silicones, styrenics, vinyls, polyesters, polyurethanes, polycarbonates, cellulosics, or proteins including collagen based materials. Furthermore, lens 40 may comprise a cell growth substrate polymer, such as those disclosed in U.S. Pat. No. 5,994,133.

Thus, in the illustrated embodiment of the invention, corneal appliance 60 comprises a lens 40 which includes a synthetic material, and more particularly, a non-donor corneal tissue material. In one embodiment, the lens is made entirely from a synthetic material. In certain embodiments, the lens is made from a combination of collagen and a synthetic material, including, combinations of bovine collagen and a synthetic material, and combinations of recombinant collagen and synthetic materials. In additional embodiments, the lens may include a poly(N-isopropylacrylamide) (polynipam) component. It has been found that a polynipam component may facilitate attachment of the lens to Bowman's membrane and/or epithelial cell layers to the lens at temperatures of about 37 degrees C. At lower temperatures, such as temperatures of about 32 degrees C, it is advantageously possible to detach the lens from the corneal tissues. For example, see Nishida, K. et al., "A novel tissue engineering approach for ocular surface reconstruction using bioengineered corneal epithelial cell sheet grafts from limbal stem cells expanded ex vivo on a temperature-responsive cell culture surface", ARVO Annual Meeting, Fort Lauderdale, Fla., May 4-9, 2003. In accordance with the present invention, the polynipam component facilitates the in viva attachment of the epithelium to the lens at substantially normal body temperatures, and may be helpful in procedures in which the lens is to be removed from the eye, by cooling of the ocular tissue.

The corneal appliance disclosed herein may provide vision correction to a subject in need thereof. In certain embodiments, the corneal appliance lens is designed to correct or reduce wavefront aberrations of a patient's eye. A wavefront aberration is the three dimensional profile of the distance between a real light wave front of a central spot of light and a reference surface, e.g., an ideal spherical shape, as shown in FIG. 1 of U.S. Pat. No. 6,585,375, and as described in Mierdel et al., "Der Ophthalmologe", No. 6, 1997. A wavefront aberration may be understood to be an optical path difference between an actual image wavefront and an ideal reference wavefront centered at an image point, at any point in the pupil of an eye. Methods of measuring wave-front aberration are well known to persons of ordinary skill in the art.

Briefly, and as described by Nader, N., *Ocular Surgery News*, "Learning a new language: understanding the terminology of wavefront-guided ablation" (Feb. 1, 2003), an aberrometer (e.g., an instrument that measures the aberrations of an eye) may be used to measure an aberrated image that leaves an eye, or may be used to measure the shape of a grid projected onto the retina. For example, while a patient is maintaining a view on a visual fixation target, a relatively narrow input laser beam may be directed through the pupil and focused onto the retina of the patient's eye to generate a point-light source on the retina. The light is reflected from the retina back through the pupil, and the wavefront of the light passing from the eye is passed to a wavefront sensor. As understood by persons of ordinary skill in the art, a wavefront can be defined as a surface that connects all field points of an electromagnetic wave that are equidistant from a light source. The light rays leave the eye and may pass through an array of lenses that detects the light rays' deviation. The wavefront gets deviated or distorted by inhomogeneities in the refractive properties in the refractive media of the eye, such as the lens, the cornea, the aqueous humor, and the vitreous humor. The resulting image is then typically recorded by a charge coupled device (CCD) camera, for example.

The wavefront is then typically reconstructed and the deviations are described mathematically in three dimensions. The wavefront deviations may be calculated, at least in part, by analyzing the direction of the light rays. Generally, parallel light beams indicate a wavefront with little, if any, aberrations, and nonparallel light beams indicate a wavefront with aberrations that do not give equidistant focal points.

Typically, Zernike polynomials are used to measure or analyze the ocular aberrations. Each Zernike polynomial describes a shape or a three-dimensional surface. As understood by persons of ordinary skill in the art, Zernike polynomials are an infinite set, but in ophthalmology, the Zernike polynomials are usually limited to the first fifteen polynomials. Second-order Zernike terms represent conventional aberrations, such as defocus and astigmatism. Aberrations above second-order aberrations are called higher-order aberrations. Higher-order aberrations typically cannot be corrected by conventional spherocylindrical lenses. Examples of higher-order aberrations include, but are not limited to, coma, spherical aberrations, trefoil (wavefronts with threefold symmetry), and quadrefoil (wavefront shapes with fourfold symmetry). Many higher-order aberrations are not symmetrical, but some higher-order aberrations, such as spherical aberrations, may be symmetrical.

In accordance with the present invention, the wavefront aberration of a patient's eye may be measured and analyzed to facilitate appropriate lens construction. The lenses of the present invention can then be shaped, as discussed herein, taking into account any wavefront aberrations. Thus, a corneal appliance is obtained with a lens body configured to correct a wavefront aberration of a patient's eye. The wavefront aberration corrective surface may be provided on either the anterior surface, the posterior surface, or both the anterior and posterior surfaces. Thus, in certain embodiments, the present lenses correct or reduce higher-order wavefront aberrations. In situations where the higher-order wavefront aberrations are asymmetrical, the lenses are configured to substantially maintain a desired orientation to correct the wavefront aberrations.

Epithelial layer 70 is fixed in position over lens 40 of corneal appliance 60. Epithelial layer 70 may comprise one or more layers of epithelial cells. The number of layers of epithelial cells are preferably between 1 and 12, and more preferably are about 5-7 layers. Thus, the number of layers of epithelium 70 closely matches the number of layers of corneal epithelium observed in vivo. The number of layers of epithelial cells may also change with time. For example, a single layer of epithelial cells may be positioned on lens 40 ex vivo, and the lens may be placed over an eye. After the procedure of placing the lens on the eye, the epithelial cells may continue to divide to form one or more additional layers of epithelial cells. Alternatively, an epithelial layer 70 may comprise approximately 5-7 cell layers when it is placed over lens 40.

Epithelial layer 70 is dimensioned to cover at least a fraction of anterior surface 42 of lens 40. In the illustrated embodiment of corneal appliance 60, epithelial layer 70 extends beyond peripheral edge 46 of lens 40. Thus, a flap or fringe of epithelium 70 extends from the edge of lens 40, which may be useful to help secure corneal appliance 60 in an eye. When epithelial layer 70 does not extend to or beyond peripheral edge 46, it is desirable to ensure that the epithelial cells either of the epithelial layer 70 or of the epithelium of the patient's eye continue to divide and migrate over the exposed portions of the lens. Suitable growth factors or other growth promoting strategies may be employed to achieve this result.

As indicated herein, epithelial layer 70 may be derived from stem cells obtained from an autologous source. In the illustrated embodiment of corneal appliance 60, epithelial layer is derived from cultured stem cells obtained from the patient receiving the corneal appliance. This is in contrast to the corneal onlay disclosed in WO 02/06883, which utilizes epithelial cells from fetal or embryonic tissue, or epithelial cells obtained from the patient receiving the corneal onlay. However, epithelial cells may also be derived from any type of stem cell that can differentiate into corneal epithelial cells, including stem cells from fetal or embryonic tissue.

In one embodiment of corneal appliance 60, the stem cells obtained from the patient are corneal epithelial limbal stem cells. The corneal epithelial limbal stem cells may be harvested, cultured, and prepared according to the methods disclosed in U.S. Patent Publication No. US 2002/0039788 A1, and by Han et al., "A fibrin-based bioengineered ocular surface with human corneal epithelial stem cells", *Cornea*, 21(5): 505-510, 2002. Briefly, corneal epithelial stem cells may be cultured onto an extracellular matrix, which may comprise basement membrane components, such as laminin, fibronectin, elastin, integrins, and collagen. Cultured epithelial stem cells are expanded on a feeder layer of replication defective, but metabolically active fibroblasts (such as 3T3 cells). After the epithelial colonies are established, the feeder cells are removed, and the epithelial cells are expanded by growth in a serum-free, low calcium medium, such as Keratocyte Growth Medium, KGM (Cascade Biologics, Oreg.). The cultured epithelial cells may then be trypsinized from their culture dish, suspended in Cornea Growth Medium, CGM (Cascade Biologics), and seeded on prepared fibrin gels. The fibrin gels are made by mixing a fibrinogen solution (plasminogen-free fibrinogen, human, Calbiochem, San Diego, Calif.) in distilled water with calcium chloride, and aprotonin (Sigma) in a buffer, such as Tris Buffer, at a pH of about 7.0, such as 7.2. Cultured corneal fibroblasts and thrombin may be added to the solution, after which, the solution is dispensed into a holder to gel.

Epithelial layer 70 is attached to anterior surface 42 of lens 40 so that epithelial layer 70 does not appreciably or noticeably move along the surface of the lens. Thus, when epithelial layer 70 and lens 40 are fixedly joined or coupled, they form corneal appliance 60. Epithelial layer 70 may be attached to lens 40 either by chemical, biological, mechanical, or electrical methods.

In certain embodiments, corneal appliance 60 may also include a cellular attachment element disposed between epithelial layer 70 and anterior surface 42 of lens 40. The cellular attachment element facilitates the stable positioning of epithelial layer 70 over lens 40. Although cellular attachment elements may be desirable when utilizing lenses fabricated from collagen, most cellular attachment components may find increased use in the hydrogel or non-hydrogel lenses described hereinabove. Cellular attachment elements may include physical perturbations of the lens 40, such as indentations provided in anterior surface 40 that facilitate cellular attachment and do not alter the optical properties of the lens. Indentations included pores that extend through the lens from the anterior surface to the posterior surface of the lens. The indentations may be provided over the entire lens or over a fraction of the lens. The indentations may also be provided in specific patterns and dimensions that facilitate cellular attachment of the epithelial layer to the lens. For example, the indentations may be provided in a plurality of concentric rings emanating from the center of the lens and expanding radially outward. Cellular attachment element may also comprise a polymer that supports adhesion of the epithelial cells to the lens. As discussed above, the lens may be made essentially from such polymers as disclosed in U.S. Pat. No. 5,994,133. In addition, these cell growth substrate polymers may be chemically bonded or otherwise coated on the surface of a hydrogel or collagen based lens to facilitate cellular attachment to the lens. The cellular attachment element may also comprise a corneal enhancer molecule, such as a corneal enhancer molecule that specifically binds to a molecule present on the extracellular surface of an epithelial cell. Examples of suitable corneal enhancer molecules include peptides, such as the tri-peptide, RGD, extracellular matrix proteins, corneal growth factors, and ligand-specific corneal enhancer species, such as laminin, fibronectin, substance P, fibronectin adhesion promoting peptide sequence, FAP, insulin-like growth factor-1 (IGF-1), k-laminin, talin, integrin, kalinin, fibroblast growth factor (FGF), and TGF-$\beta$, as disclosed in U.S. Patent Publication No. US 2002/0007217 A1. These corneal enhancer molecules may include a tether, which may enhance the ability of epithelial cells to attach and migrate over the lens 40.

As indicated above, lens 40 of corneal appliance 60 may be made from collagen to mimic a native corneal stroma, a hydrogel, or a biocompatible non-hydrogel material. The lens of corneal appliance 60 may be produced according to standard techniques known to those skilled in the art. As indicated above, when stromal-like lenses are desired, a collagen matrix may be formed and include stromal cells. Lens 40 may be shaped in a conventionally dimensioned mold suitable for lenses, such as corneal onlays. For example, lens 40 may be ablated, molded, spin-casted and/or lathed, or combinations thereof. However, because it may be desirable to culture the epithelial cells on lens 40, the molds used to manufacture corneal appliance 60 may be structured to permit nutrient, liquid, and gas exchange with the cultured cells. For example, a mold may comprise one or more pores to permit nutrients and liquid and gas to flow to the cell culture. The molds may be made from any suitable, porous material, including, but not limited to, ceramics, mesh, such as stainless steel mesh, or membranes made from nylon, cellulose, or the like. In one embodiment, the mold may comprise a concave surface and a convex surface matingly shaped with respect to each other. The mold may be able to be placed in a well having culture medium to facilitate the culturing of the cells. The shape of the lens may be determined by the mold designed for culturing (hereinafter referred to as the culturing mold), or may be shaped in a conventional mold. If shaped in a conventional mold, the lens may then be subsequently placed in a culture dish having a desired shape to preserve the shape of the lens, where the culture dish is structured to facilitate the culturing of the epithelial cells.

Epithelial cell layer 70 may be prepared essentially as described above. In short, a fibrin matrix, or other extracellular protein matrix, may be produced from serum and the corneal epithelial stem cells may be seeded in the matrix. The seeded matrix may then be applied on the anterior surface of the lens. The cells may be applied by dispensing the matrix over the surface of the lens, or the cells may be applied as a relatively flexible layer of cells or a film of cells that sufficiently flexes to accommodate the curvature of the lens. The film of cells may comprise a film of corneal epithelial stem cells or a film of developed epithelial cells, which may be one or more layers thick, or a combination thereof.

Alternatively, a layer of epithelial cells may be obtained by culturing immortalized human corneal epithelial cells, such as disclosed in U.S. Pat. No. 6,284,537. With such cell lines it is desirable to regulate cell growth once the corneal appliance is placed on the eye. Cell growth may be regulated using any conventional method known by persons of ordinary skill in the art.

In another embodiment, the epithelial cell layer may be a layer or flap of epithelial cells of the patient that has been separated from the patient's cornea, as described herein. The preformed layer of epithelial cells may be placed over the lens body after the lens body has been placed over the cornea. The lens body may or may not have received a surface treatment to help the layer of epithelial cells to attach to the lens body. For example, when lens bodies are used that are made from polymeric materials or composites that promote cellular attachment, it may not be necessary to include a surface treatment on the lens body.

In addition, one embodiment of the corneal appliance includes a suspension of epithelial stem cells provided on the anterior surface of the lens body. The suspension may be a fibrin-based suspension, as disclosed herein. It is believed that the epithelial stem cells that are provided over the lens body may provide nutrients, such as growth promoting factors, that promote attachment of the layer of epithelial cells to the lens body. Thus, a suspension of stem cells is provided over the lens body and the flap of epithelium is placed over the lens body, and the stem cells encourage attachment and growth of the epithelial cells of the flap over the lens body. Surprisingly, the stem cells survive for a sufficient amount of time when placed on the lens body to promote the attachment of the epithelial cell layer to the lens body.

In a further embodiment, corneal appliance 60 may be manufactured by molding a synthetic material, such as recombinant collagen, in a lens mold having a desired structure to correct a visual deficiency. The collagen lens may be populated with stromal keratocytes that have low antigenicity or immunogenicity. The collagen lens may be modified on its surface to promote cellular attachment of the epithelial cells, and then a culture of epithelial stem cells may be placed on the collagen lens where they can grow and differentiate into an epithelial cell layer.

Figure 5A:
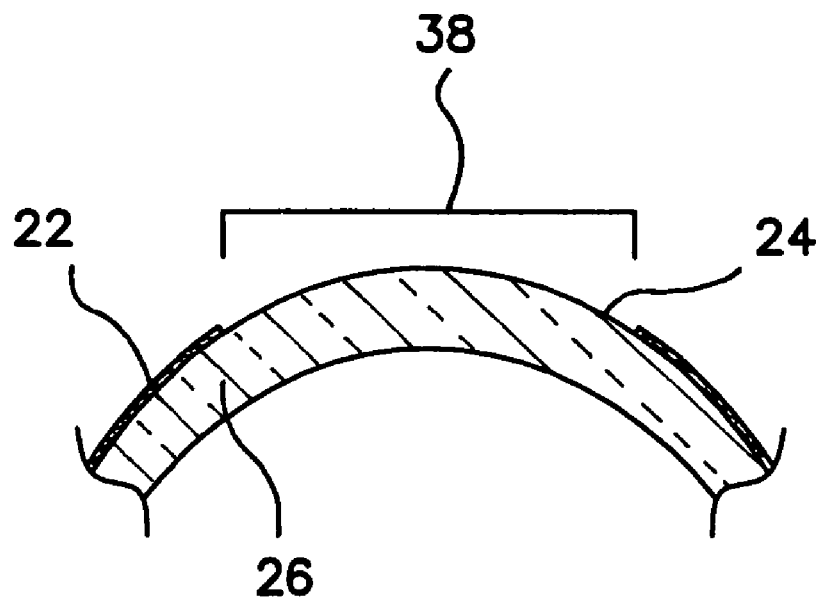
FIG. 5A is a diagram of a magnified sectional view of a deepithelialized cornea.

Corneal appliance 60 may be placed over an eye to provide the desired vision correction. Because corneal appliance 60 includes a layer of epithelium, as described hereinabove, it is desirable to remove at least a portion of the epithelium from the patient's eye receiving the appliance. The deepithelialized portion should at least have approximately the same dimensions as the corneal appliance. A deepithelialized cornea is illustrated in FIG. 5A.

The epithelium may be removed by any conventional method. For example, an abrasive device can be used to remove the epithelium, a small rotating brush may be used, sterile cocaine may be applied to the epithelium, an alcohol wash, such as an ethanol wash, may be used alone or in combination with a source of electromagnetic energy on the epithelium, such as with the LASEK and LASIK procedures, which are well known. In addition, a portion of the epithelium may be removed using a separator that can separate the epithelium from Bowman's membrane to form a pre-formed layer of epithelial cells. One example of a separator is a sub-epithelial separator developed by Dr. Ioannis Pallikaris (Greece), such as the separator disclosed in U.S. Patent Publication Nos. 2003/0018347 and 2003/0018348. The separator may include a suction device, or ring, that can deliver suction to the epithelium to cause the epithelium to be lifted from the cornea. A cutting device, such as a blade, including a microkeratome, which may or may not be a part of the separator can then be used to cut the portion of the epithelium that is being lifted from the cornea to create a flap, or to completely remove that portion of the epithelium that is being manipulated. Alternatively, or in addition, the separator can include a temperature controller that causes temperature changes in a portion of the device that contacts the epithelium. The separator may be cooled to cause the epithelium to attach to a cooled region of the separator so that it may be lifted from the cornea, and then may be warmed, passively or actively to allow the epithelial tissue that has been cut to be released from the separator. It has been found that the temperature control enables the handling of the epithelial cells of the epithelium without undue damage and cellular injury to the epithelial cells during the procedure. It appears that the cooling not only provides a convenient way of attaching the epithelium to the separator, but that the cooling provides protection to the cells that are being manipulated during the manipulation procedure. When electromagnetic energy is used as the epithelial cutting device, it may be desirable to use an electromagnetic energy source, such as a laser, with reduced, and preferably no, thermal energy to help reduce cellular injury during the procedure. For example, a fluid, such as water or saline, may be used in conjunction with the electromagnetic energy to reduce thermal damage caused by the electromagnetic energy. When removing the corneal epithelium, it may be desirable to remove one or more small portions of Bowman's membrane, as indicated herein to facilitate more rapid healing of the ocular tissue. However, in certain situations, the Bowman's membrane is left entirely intact.

Figure 5B:
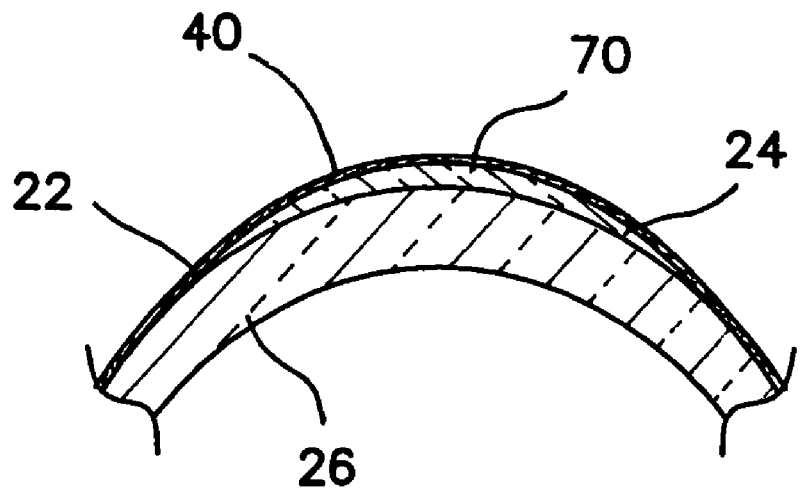
FIG. 5B is a diagram of the deepithelialized cornea of FIG. 5A with a corneal appliance placed over the cornea.

Once the desired amount of epithelium is removed, corneal appliance 60 may be placed on the deepithelialized cornea. When the lens of the appliance is made from collagen, the lens may make a natural bond with the Bowman's membrane that holds the lens in place on the eye. However, additional adhesive mechanisms may be used to facilitate securing the appliance on the eye. For example, glue, preferably a biodegradable glue, may be applied to the overlying fringe of epithelium 70, dissolvable sutures may be used to secure the fringe of epithelium to the eye, or pressure applied by a bandage can be used to hold the appliance in place until the epithelium has bonded with the rest of the eye. Additionally, or alternatively, a fibrin-based stem cell matrix may be applied as an adhesive to help maintain the placement of the epithelium and to promote healing and development of the epithelium. Once the surgery is complete, the epithelium of appliance 60 blends together with any remaining corneal epithelium that remains on the eye, as shown in FIG. 5B. Thus, corneal appliance 60 has a layer of epithelium that is more reliably or consistently attached to the lens body than an epithelium that is attached to a lens body obtained from donor tissue, such as disclosed in PCT Publication No. WO 02/06883.

Corneal appliance 60 may provide a substantial improvement in the field of corrective vision technology. The appliance is a device that provides long-term vision correction that can be reversed, as opposed to procedures that permanently alter the shape of a patient's cornea, such as LASEK and LASIK procedures. In that regard, the corneal appliance may be easily removed from the patient if complications develop or the patient's vision changes. Thus, corneal appliance 60 provides for long-term, but reversible, vision correction.

By way of example, and not by way of limitation, a procedure for improving a patient's vision may begin by a patient with a vision defect visiting a physician. The physician harvests a sample of corneal epithelial stem cells from the patient and sends the sample of cells to a lab for culturing. In the lab, the cells are seeded and cultured in a fibrin matrix, as described above, and are applied to the anterior surface of a lens. The lens may be treated or modified on its anterior surface to promote cellular attachment of the epithelial cells. The surface treatment may include physical perturbations, such as roughening of the lens surface, or may include providing the lens with one or more cellular attachment elements, as discussed hereinabove. After approximately 10-20 days, the cultured cells have developed into a layer of epithelial cells that substantially covers the entire surface of the lens. The corneal appliance may then be delivered to the physician's office. The patient returns to the physician's office for the procedure, which includes removing the epithelium from the patient's cornea and applying the corneal appliance to the deepithelialized cornea. Preferably, the epithelium is only removed to the Bowman's membrane, and is removed so that the diameter of the deepithelialized portion of the cornea corresponds to the diameter of the epithelial layer of the corneal appliance.

Figure 6A:
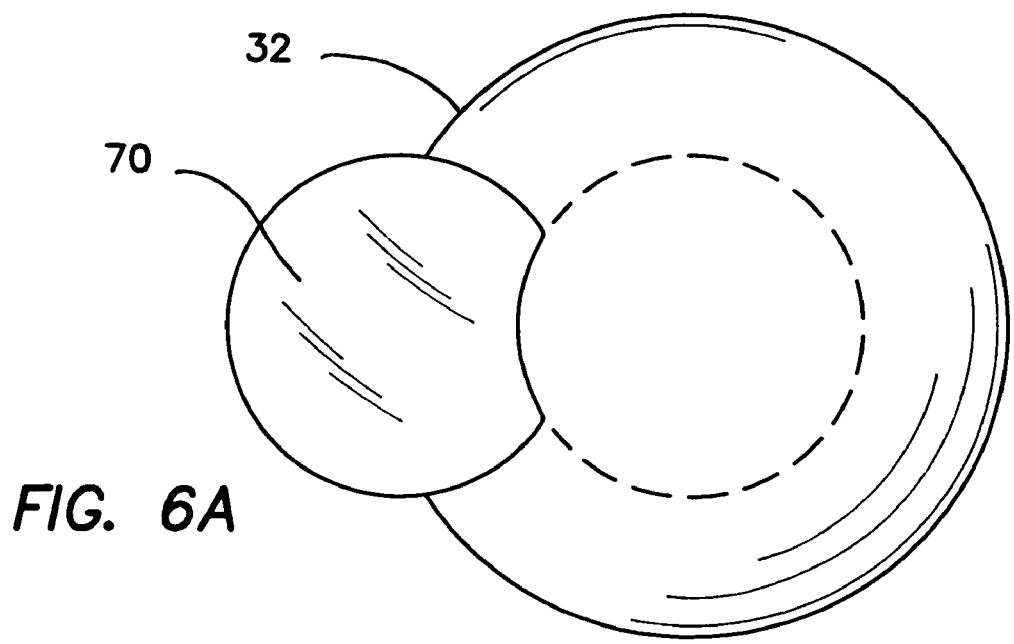
FIG. 6A is an illustration of a front plan view of an eye in which a preformed epithelial cell layer is formed as a flap.
Figure 6B:
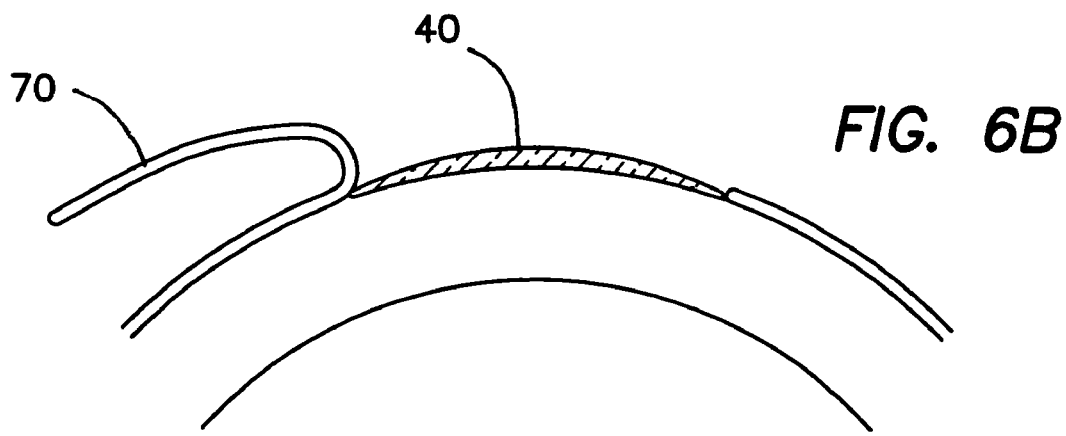
FIG. 6B is a sectional view of the eye of FIG. 6A.
Figure 6C:
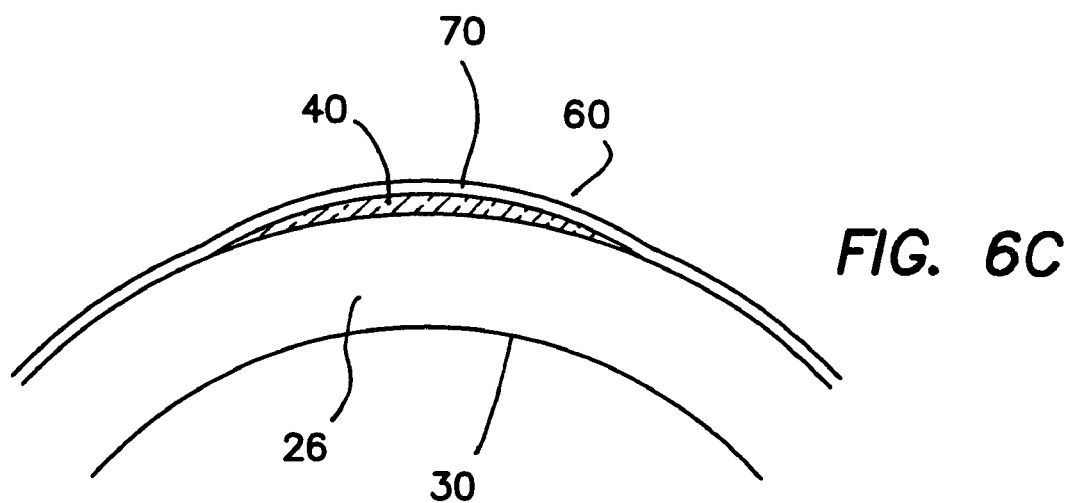
FIG. 6C is a sectional view similar to FIG. 6B in which a lens has been placed on the deepithelialized eye and the preformed layer of epithelium has been placed over the lens.
Figure 7A:
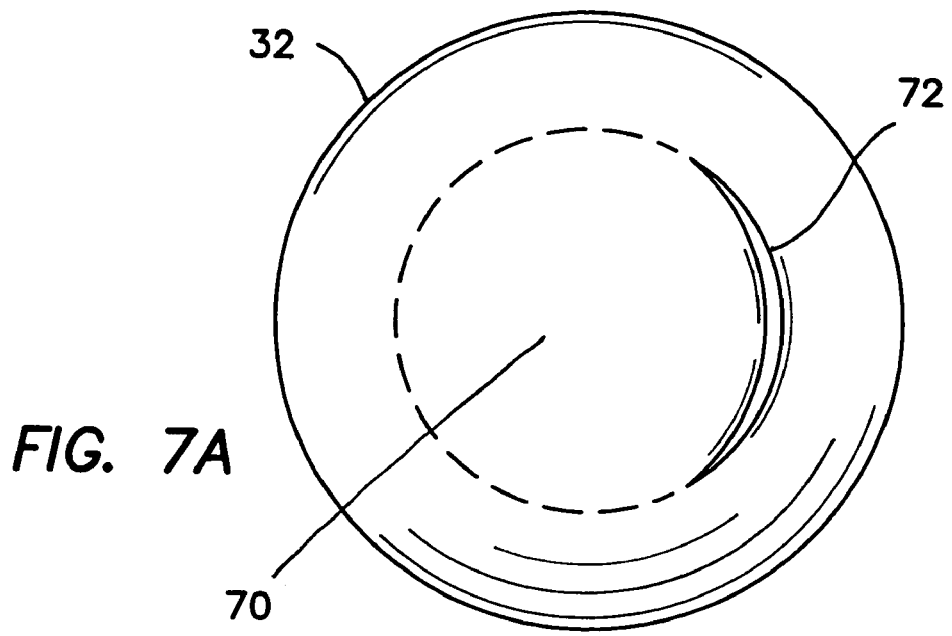
FIG. 7A is an illustration of a front plan view of an eye in which a preformed epithelial cell layer is formed as a pocket.
Figure 7B:
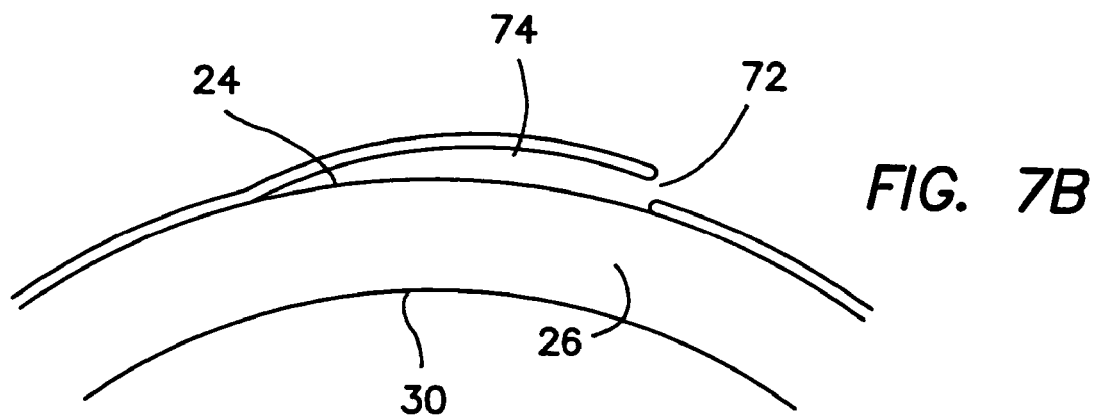
FIG. 7B is a sectional view of the eye of FIG. 7A.
Figure 7C:
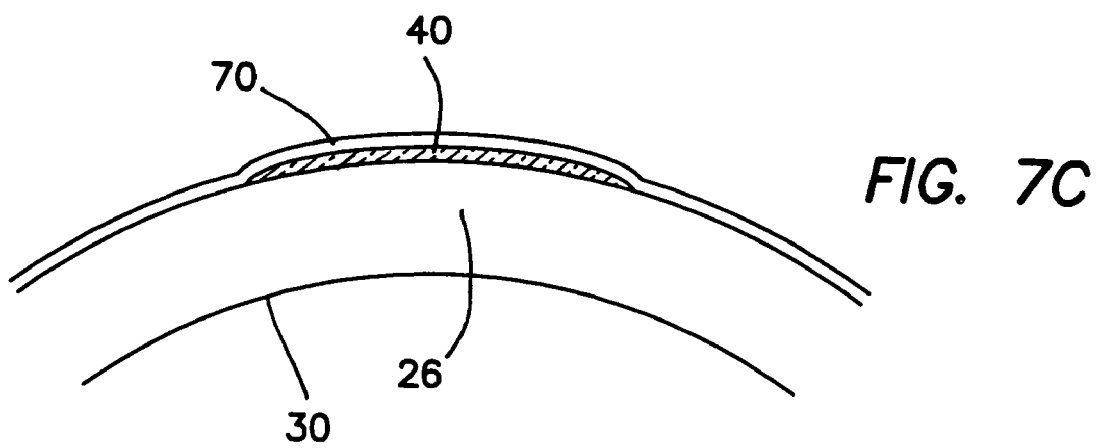
FIG. 7C is a sectional view similar to FIG. 7B in which a lens has been placed in the pocket.

In addition, another method of improving a patient's vision includes creating a slit, incision, or opening in the patient's corneal epithelium that is large enough to permit a lens, as described above to be inserted into through the slit underneath the epithelium, as shown in FIGS. 7A, 7B, and 7C. After the slit 72 is formed, the epithelium may be separated from the Bowman's membrane using standard blunt dissection techniques or other conventional methodology to form preformed epithelial cell layer 70. Alternatively, the corneal epithelium may be separated from the cornea using a separator, as discussed above. The epithelium may be separated to form a flap of tissue (FIGS. 6A, 6B, and 6C), or may be separated to form an epithelial pocket, such as pocket 74 shown in FIG. 7B, without forming a flap. The lens 40, which may or may not be surface treated to promote cellular attachment, may be inserted under the flap, or into the pocket created between the epithelium and Bowman's membrane. After the lens is in position, and the layer of epithelium is replaced over the lens, an adhesive, such as a corneal epithelial layer derived from stem cells, or a stem cell suspension, as disclosed hereinabove, may be applied to the slit region of the patient's epithelium to promote the healing of the incision.

In accordance with the method disclosed hereinabove, a method of correcting or improving vision includes a step of inserting a vision correcting ocular device, for example, a corrective lens or lens body, beneath the epithelium of a patient's cornea substantially without uncovering or exposing an anterior surface of the cornea located under the epithelium, such as shown in FIGS. 7A, 7B, and 7C. The anterior surface of the cornea may be Bowman's membrane, or it may include one or more portions of the corneal stroma. This method is in contrast to techniques that produce a flap of epithelial tissue to expose or uncover an anterior surface of the cornea, as discussed herein, and as shown in FIGS. 6A, 6B, and 6C. By inserting an ocular device beneath an epithelium but on or above the stroma or Bowman's membrane, the ocular device is effectively substantially fixedly positioned with respect to the eye, for example, by the epithelium, to provide the desired vision correction. In addition, this method provides for relatively enhanced healing or reduced times and reduced side effects relative to methods that produce a flap of epithelial tissue to insert an ocular device.

Figure 8A:
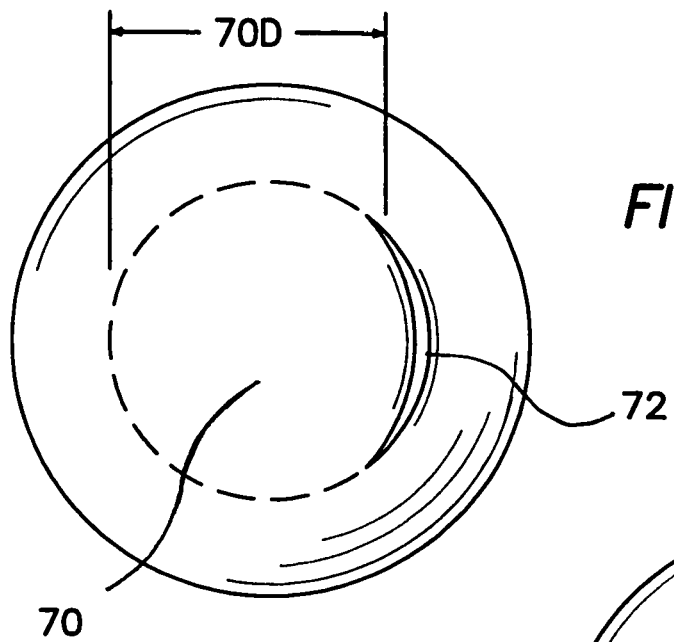
FIG. 8A is an illustration of a front plan view of an eye with a relatively large incision.
Figure 8B:
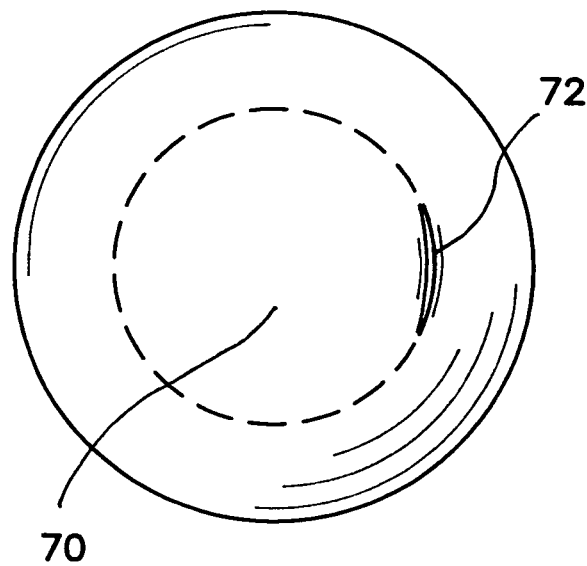
FIG. 8B is similar to FIG. 8A with a smaller incision.
Figure 8C:
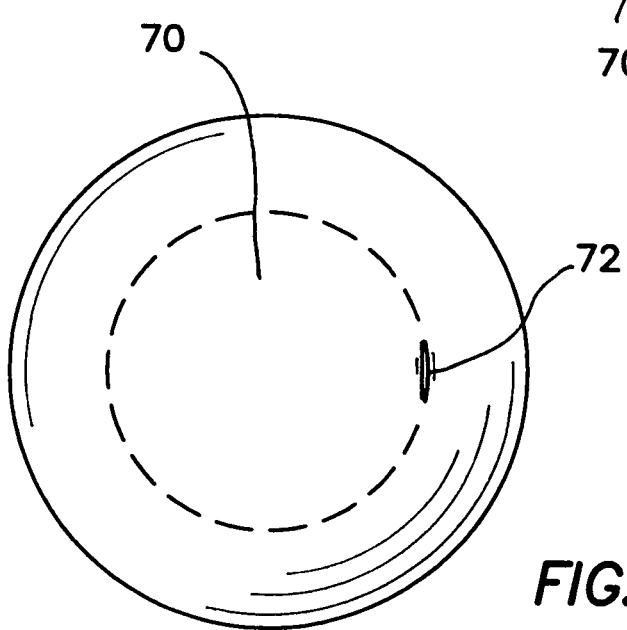
FIG. 8C is similar to FIG. 8B with a smaller incision.

In one aspect of the foregoing method, the lens may be inserted by inserting the ocular device through an incision formed in the epithelium. An incision may be formed at any desired region around the epithelium, but in preferred embodiments, the incision or incisions is formed either in the temporal portion of the epithelium (e.g., the portion of the epithelium that is located away from the nose of a patient), or in the medial portion of the epithelium. The incision is preferably formed to provide an opening in the epithelium, for example, of suitable size, to accommodate a corrective ocular device to be inserted therethrough without creating an epithelial flap. By forming incisions of different sizes, the preformed epithelial layer diameter 70D may also vary, as shown in FIGS. 8A, 8B, and 8C. For example, a relatively large incision 72 as shown in FIG. 8A may provide a relatively small preformed epithelial diameter 70D. In addition, or alternatively, the incision size may be varied to accommodate various insertion techniques, such as whether a lens is deformed prior to insertion. Thus, a large incision may be formed when a lens is inserted in a substantially undeformed state, or a small incision may be formed when a lens is inserted in a deformed state.

In certain embodiments, it is desirable to form a relatively small incision, and deforming the ocular device prior to insertion through the incision so that the deformed ocular device is inserted through the incision beneath the epithelium. After being placed under the epithelium, the deformed ocular device can assume its native or original configuration (e.g., the configuration of the ocular device before being deformed). For example, an incision 72 may be made in the epithelium of an eye, as shown in FIG. 11A and FIG. 11B. The lens 40 may then be "rolled", as shown in FIG. 11C, or "folded", as shown in FIG. 11D so that the lens can be inserted in the incision 72. For example, the lens 40 shown in FIG. 11D is folded along its midline so that two substantially equal-sized portions overlap. The deformed lenses may then be inserted into the incision 72 as indicated herein.

The incision can be made by cutting or slicing the epithelium using a sharp instrument, such as a microkeratome and the like, including the microkeratome disclosed hereinabove. Alternatively, or in addition, the incision can be made by using blunt dissection to separate epithelial cells to create an opening in the epithelium without cutting or slicing the epithelium. Blunt dissection provides an advantage of reduced injury to the epithelial cells and/or epithelial tissue.

To perform blunt dissection, a blunt shaped instrument is used that has a thickness that reduces the potential for tearing the epithelium as it is being separated from Bowman's membrane, and for damaging Bowman's membrane of the corneal stroma. One suitable blunt dissector includes a plate, a wire, or a knife with a dull edge. A spatula is also a suitable blunt dissection apparatus. The blunt dissector is inserted under the epithelium and is gently urged across the underlying corneal surface to "tease" the epithelium from Bowman's membrane. The separation appears to follow a path of least resistance to provide a substantially complete separation of the epithelium from Bowman's membrane substantially without damaging either the epithelium or the underlying cornea. Separation proceeds across the surface of the cornea to obtain a void sized to accommodate a corrective ocular device.

In certain embodiments, only one incision is made in the epithelium, but in additional embodiments, two or more incisions can be made in the epithelium to permit insertion of the ocular device. When multiple incisions are made, the incisions may be parallel to each other or may be orthogonal to each other. In certain embodiments, two incisions may be made that intersect to form four flaps of epithelial tissue.

As discussed herein, the ocular device may be a vision correcting lens, such as a corneal onlay. The ocular device may comprise a synthetic material, including a synthetic polymeric material, as discussed above. In certain embodiments, the ocular device may be a contact lens that is structured to be placed between the epithelium and Bowman's membrane of the cornea.

To insert the ocular device in accordance with the foregoing method, a portion of the epithelium may be lifted or spaced apart from the cornea. An incision may be made in the epithelium after the portion of epithelium has been lifted or spaced apart. An incision is preferably made in the raised or lifted portion; however, in certain embodiments, an incision may be made in a region of the epithelium that is located at a site spaced apart from, but in proximity to, a site at which the epithelium begins to be spaced apart from Bowman's membrane.

The ocular device may then be inserted through the incision. The ocular device may be inserted by using forceps, or other similar device. Or, the ocular device may be inserted by using an inserter that is configured to deform at least a portion of the ocular device so that the device can fit through the incision, for example, through a smaller incision that would be necessary if the ocular device was not deformed. For example, the ocular device may be folded or rolled or curled so that its cross-sectional area is reduced while it is being inserted beneath the epithelium, as discussed herein. A corneal onlay insertion device may be a syringe like device which includes a body with a distal end dimensioned to pass the lens under the corneal epithelium of an eye. In certain situations, the corneal onlay insertion device may be similar, or at least somewhat similar, to well known and publicly available intraocular lens inserters.

Figure 9A:
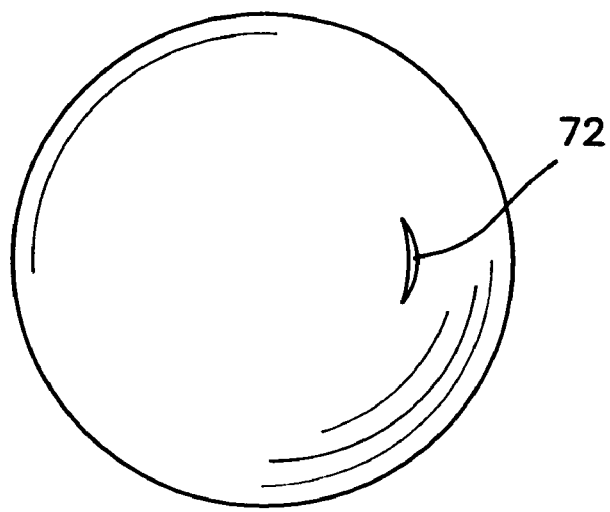
FIG. 9A is an illustration of a front plan view of an eye with a relatively small incision in the epithelium.
Figure 9B:
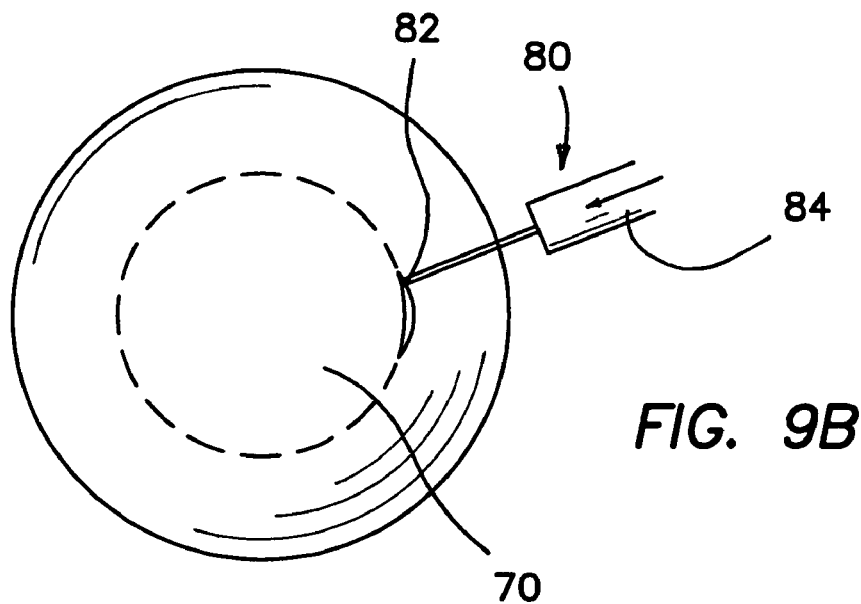
FIG. 9B is a view similar to FIG. 9A in which a fluid injector is inserted into the incision in the epithelium to deliver fluid therebeneath.
Figure 9C:
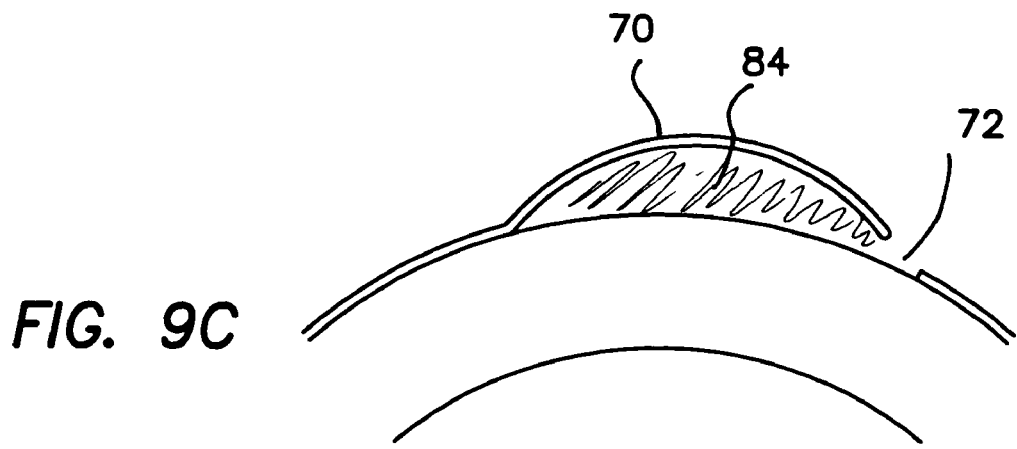
FIG. 9C is a sectional view of the eye of FIG. 9B after the fluid has been delivered beneath the epithelium.
Figure 9D:
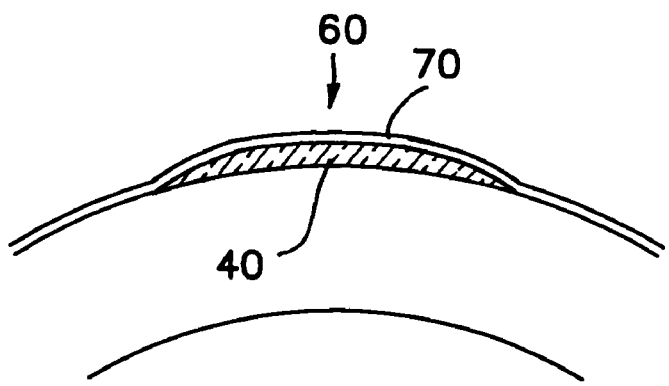
FIG. 9D is a sectional view similar to FIG. 9C in which a lens has been inserted beneath a preformed epithelial cell layer.

The epithelium may be raised using any suitable technique that permits the epithelium to be separated from Bowman's membrane preferably without substantially damaging Bowman's membrane or the corneal stroma. In certain embodiments, a portion of the epithelium is raised using a vacuum. The vacuum may be provided with a microkeratome, such as with the separator disclosed in U.S. Patent Publication Nos. 2003/0018347 and 2003/0018348, or it may be provided as a separate instrument. Alternatively, or in addition, the epithelium may be lifted by delivering a fluid beneath a portion of the epithelium, as shown in FIGS. 9A, 9B, 9C, and 9D. For example, a small incision 72 may be made in the epithelium of an eye, as shown in FIG. 9A. A syringe device 80 having a distal end 82 and a fluid 84 located in the body of the syringe device may be placed in proximity to the eye so that the distal end 82 can pass the fluid 84 beneath the epithelium of the eye, as shown in FIG. 9B. The fluid 84 causes the preformed layer of epithelium 70 to be separated from the stroma of an eye, as shown in FIG. 9C. A lens 40 may then be placed under epithelium 70, and as the fluid 84 decreases in volume, the epithelium 70 is placed over the lens 40 to form corneal appliance 60, as shown in FIG. 9D. The delivery of fluid causes the epithelium to swell to create a bulge of epithelial tissue that is spaced apart from Bowman's membrane, as indicated above. One suitable fluid may include sodium chloride, for example, an aqueous sodium chloride solution. Another fluid may include a gel. The gel may be a gel that includes at least one water soluble or water swellable polymeric material, for example, at least one cellulosic component, such as hydroxymethylcellulose and the like, and/or one or more other water soluble or water swellable polymeric materials. In one specific embodiment, the fluid comprises a gel sold as GENTEAL gel by CibaVision, Duluth, Ga.

In preparing the epithelium for insertion of an ocular device in accordance with the invention herein disclosed, an effective amount of a preserving agent may be applied to the epithelium to reduce cellular injury and death, and to preserve the epithelium in a viable state. The preserving agent may act as a moisturizer to maintain the epithelium in a moisturized state. The epithelium preserving agent maybe include a gel, and in certain embodiments, the epithelium preserving agent comprises a component selected from the group consisting of water soluble polymeric materials, water swellable polymeric materials, and mixtures thereof. In further embodiments, the epithelium preserving agent includes at least one cellulosic component. In still further embodiments, the epithelium preserving agent includes hydroxymethylcellulose. One suitable epithelium preserving agent is the GENTEAL gel identified above.

In another aspect of the present invention, a method for correcting or improving vision includes raising a portion of an epithelium of a cornea of an eye away from Bowman's membrane, cutting a portion of the epithelium to create an elongate incision in the epithelium substantially without damaging the Bowman's membrane, and inserting a corrective ocular device through the incision so that the ocular device is located between the epithelium and Bowman's membrane. As indicated above, the epithelium may be raised using a vacuum, a liquid, or any other suitable device. Liquids used to raise the epithelium may include sodium chloride and/or other tonicity agents. In certain embodiments, the liquids are hypertonic aqueous liquids. In one specific embodiment, the liquid is an aqueous solution containing about 5% (w/v) of sodium chloride.

One or more incisions may be made in the epithelium using a cutting procedure or blunt dissection procedures, as discussed above. Importantly, in this aspect of the invention, the epithelium is cut without forming an epithelial flap. In addition, the ocular device is inserted beneath the epithelium substantially without uncovering or exposing an anterior surface of Bowman's membrane. The method may be practiced by applying one or more epithelial preserving agents to the epithelium. In practicing this method of the invention, the stroma of the cornea is preferably maintained in a substantially intact or undamaged state.

In yet another aspect of the present invention, a method for correcting or improving vision includes applying a liquid to the epithelium of a cornea of an eye to loosen the epithelium substantially without killing or otherwise devitalizing epithelial cells, treating the epithelium to provide and/or maintain the epithelium in a moisturized state, raising a portion of the loosened epithelium from a surface of the cornea located below the epithelium, separating the raised portion of the epithelium from the surface of the cornea, forming one or more elongate incisions in the raised portion of the epithelium, and inserting a corrective ocular device beneath the epithelium through the one or more elongate incisions.

The method may also include a step of delivering a substance beneath the raised portion of the epithelium to maintain a spaced apart relationship between the epithelium and the surface of the cornea, prior to forming an incision in the epithelium.

Suitable liquids for loosening the epithelium without devitalizing or killing epithelial cells include sodium chloride and/or other tonicity agents, for example, in aqueous solutions. In one embodiment, the liquid is a hypertonic aqueous liquid.

The methods disclosed herein may also be practiced by scoring a portion of the epithelium to create an epithelial defect prior to applying the liquid. The treating step of the foregoing method may include applying a gel to the epithelium, such as a gel that contains a water soluble polymeric material, a water swellable polymeric material, or combinations or mixtures thereof. One suitable gel includes at least one cellulosic component, such as hydroxymethylcellulose, and the like and mixtures thereof.

Similar to the methods disclosed hereinabove, the epithelium may be raised or lifted using a vacuum, or other appropriate device, and the epithelium may be separated using a blunt dissection device, such as a spatula or wire. The gel-containing composition identified above may also be delivered beneath the raised epithelium to maintain the epithelium in a spaced apart relationship from Bowman's membrane.

Figure 10A:
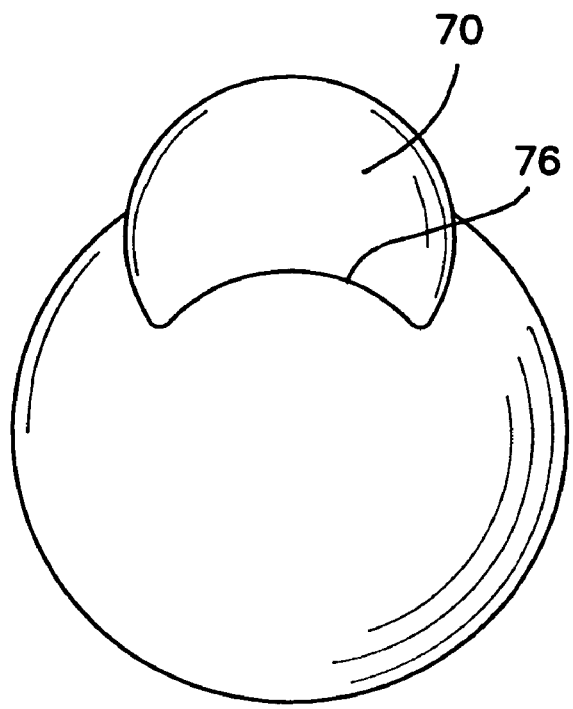
FIG. 10A is a front plan view of an eye having an epithelial flap with an superiorly located hinge portion.
Figure 10B:
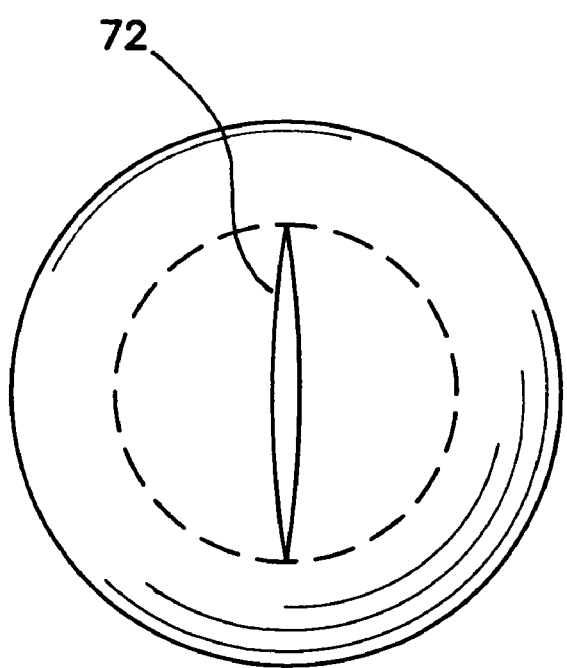
FIG. 10B is a front plan view of an eye having a central epithelial incision.
Figure 10C:
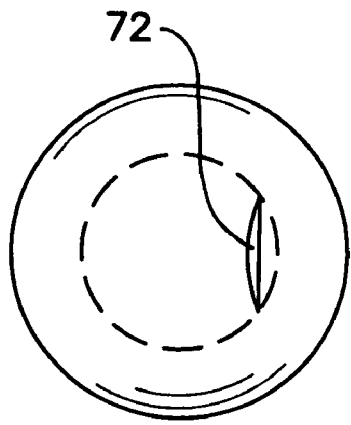
FIG. 10C is a front plan view of an eye having an offset epithelial incision.
Figure 10D:
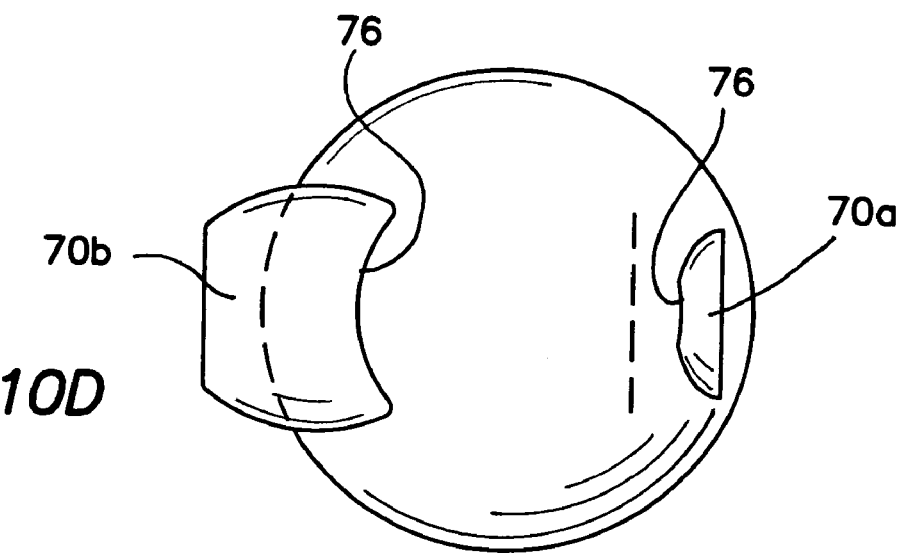
FIG. 10D is a front plan view similar to FIG. 10C in which an offset incision is used to form two flaps with offset hinge portions.
Figure 10E:
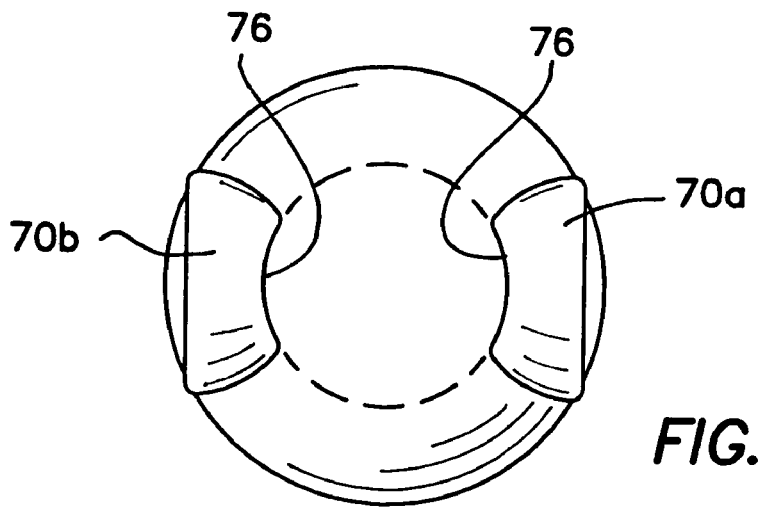
FIG. 10E is a front plan view similar to FIG. 10B in which a central epithelial incision is used to form two flaps with offset hinge portions.

Incisions are formed in practicing this method using a microkeratome to cut or slice one or more portions of the epithelium. In practicing this method, incisions are made in the epithelium to create or form one or more epithelial flaps which are hinged portions of epithelial tissue that can be folded or rolled back, or positioned to expose an underlying surface of the cornea. In one embodiment, a single incision is made in the epithelium to create a flap 70 of epithelium that includes a hinged portion 76 located at the periphery of the eye, as shown in FIG. 10A, where the hinged portion is located in a superior region of an eye. As shown in FIG. 10B, a medial incision 72 may be formed, and two flaps 70a and 70b (FIG. 10E) may be obtained with hinge portions 76 offset from a medial position of the eye. In addition, as shown in FIG. 10C, an incision 72 may be formed away from the medial portion of the eye, such as at a temporal region of the eye. This offset incision may then be used to form two flaps 70a and 70b as shown in FIG. 10D with hinge portions 76 offset from a medial region of the eye. In preferred embodiments, the incision is formed offset from the pupil of the eye to reduce potential injury to the cornea above the pupil. In another embodiment, a plurality of incisions are made in the epithelium to form a plurality of flaps that can each be folded back to expose an underlying surface of the cornea. For example, a substantially vertical incision can be made along the midline of the eye, and a substantially horizontal incision can be made to intersect the vertical incision to create four flaps of epithelial tissue.

After the incisions are made, an ocular device is inserted on the exposed underlying corneal surface, and the flaps of tissue are replaced over the ocular device.

As indicated elsewhere herein, the ocular device is preferably a vision correcting lens, and in certain embodiments, the ocular device is a contact lens that is structured to be placed under the epithelium of a cornea of an eye. In additional embodiments, the ocular device is a corneal onlay.

In one specific embodiment, a method of correcting or improving vision in accordance with the invention disclosed herein may be performed by scoring the epithelium to make a small, linear, 1- to 2-mm epithelial defect, similar to a small scratch in the epithelium. Next, a tonicity component, such as 5% sodium chloride, is applied for 10 seconds over the entire cornea. The tonicity component is effective to stiffen and loosen the epithelial cells without killing them. The tonicity component may then be rinsed away. The epithelium is kept moist using a moisturizer or epithelial preservative. Examples of suitable moisturizers or epithelial preservatives include water swellable polymers and/or water soluble polymers, as discussed above. One example of a suitable moisturizer is GENTEAL gel (hydroxymethylcellulose 0.3%; CIBA Vision, Duluth, Ga.).

A microkeratome suction ring may then be placed onto the limbus, and centered over the cornea. While the pressure on the eye is raised, a spatula or other blunt dissection device (e.g., as sold by Mastel Precision Surgical Instruments, Rapid City, S.D.) is used to slip through the small linear epithelial defect, and mechanically strip off epithelial cells, for example an epithelial cell layer, using a "spatulating" or blunt dissection technique. The suction ring is typically applied for less than 30 seconds, and not more than twice for a given procedure. The epithelium is then filled with a substance to raise the epithelium into a gumdrop-like shape, away from Bowman's layer. One suitable substance is GENTEAL gel.

Next, a version of the butterfly LASEK technique may be performed, for example by making an incision down the middle of the epithelial "gumdrop," and pushing the two halves aside. If one cut is not sufficient to expose Bowman's layer and to accommodate the corrective ocular device, one or more additional incisions can be made in the epithelial sheet to form multiple quadrants (e.g., four) of epithelial tissue. The flaps or quadrants of epithelial tissue may then be laid back over the limbus, out of the way of the ocular device to be inserted. Before inserting the ocular device, the gel may be rinsed away with a moist cellulose sponge, being careful not to damage the epithelial sheet. The epithelial layers may then be folded back into place over the corrective ocular device. The epithelium may then be covered and/or may receive one or more healing agents, which may include antimicrobial components to promote healing of the epithelium.

In practicing the foregoing methods in which the epithelium is raised and one or more elongate incisions are made in the raised portion, the step of treating the epithelium to provide and/or maintain the epithelium in a moisturized state may be omitted, and the method may include a step of delivering a substance beneath the raised portion of the epithelium to maintain a spaced apart relationship between the epithelium and the surface of the cornea.

The foregoing methods may also include a step of applying a healing agent to the epithelium to promote a more rapid and effective healing of the epithelium after insertion of the lens. In certain embodiments, the healing agent includes an antimicrobial, for example, selected from such materials which are conventional and/or well known for use in ophthalmic applications, to reduce potential contamination and infection. The healing agents may be any suitable ophthalmic composition which promotes cellular growth, such as epithelial cell growth, and/or reduces cellular death.

Still further in accordance with the invention disclosed herein, a reversible vision correction procedure has been invented. The method includes a step of inserting a corrective ocular device beneath an epithelium of a cornea of an eye, preferably, substantially without damaging Bowman's membrane of the cornea, and a step of removing the corrective ocular device from the eye. Among other things, if a patient finds that the corrective ocular device is or becomes insufficient to provide the desired vision correction, or is otherwise unsatisfactory in performance or comfort, the ocular device can be removed, and the patient's vision can be returned to its previous state. Thus, a patient can experience an improvement in vision similar to that provided by current LASIK and LASEK procedures, but with the advantage of being able to restore the patient's vision if the patient or physician is not completely satisfied with the vision correction.

The method may also include another step of inserting another corrective ocular device after the first ocular device is removed. For example, if the correction provided by the first ocular device is not sufficient to adequately improve the patient's vision, a second ocular device with different vision correcting properties may be inserted to obtain the desired vision correction.

In practicing the foregoing methods, the corrective ocular device is preferably a vision correcting lens, however, other suitable devices that may augment the focusing capabilities of the eye may be utilized. The ocular device may be inserted under the epithelium by forming one or more epithelial flaps, or by forming an incision without forming an epithelial flap, as disclosed above. In certain embodiments, a moisturizer or epithelial preserving agent is administered to provide and/or maintain the epithelium in a moisturized state. The epithelial preserving agent may be a gel-like composition including a water soluble polymeric material, a water swellable polymeric material, and/or mixtures thereof, as disclosed above. The incisions in the epithelium can be made by cutting the epithelium by using a microkeratome or similar instruments, or by separating the epithelial tissue without devitalizing the epithelial tissue, such as by using a blunt dissector, as disclosed above.

While this invention has been described with respect to various specific examples and embodiments, it is to be understood that the invention is not limited thereto and other embodiments are within the scope of the invention.

A number of publications and patents have been cited hereinabove. Each of the cited publications and patents are hereby incorporated by reference in their entireties.

What is claimed is:

1. A method for vision correction of an eye having a corneal epithelium and a Bowman's membrane disposed under the corneal epithelium, the method comprising:
separating the corneal epithelium from the Bowman's membrane to form an epithelial cell layer separated from the Bowman's membrane and a pocket extending between the epithelial cell layer and the Bowman's membrane, the epithelial cell layer separated from the Bowman's membrane having a periphery substantially attached to the Bowman's membrane to fix a lens to the eye; and
inserting the lens into the pocket between the epithelial cell layer and the Bowman's membrane of the eye, such that the lens is substantially fixed on the Bowman's membrane of the eye with the epithelial cell layer.

2. The method of claim 1, further comprising forming an incision in the epithelium to create the pocket.

3. The method of claim 2, wherein the step of forming an incision includes forming an incision on an approximate nasal portion, a temporal portion, a superior portion, and/or inferior portion of the epithelium.

4. The method of claim 2, wherein the step of forming an incision includes forming an incision on an approximate medial portion of the epithelium to form a first pocket and a second pocket, each pocket sized to accommodate a portion of the lens.

5. The method of claim 1, further comprising deforming the lens prior to the inserting step.

6. The method of claim 1, further comprising removing the lens from the eye, and inserting another vision correcting lens into the pocket.

7. The method of claim 1, wherein the lens comprises a synthetic material.

8. The method of claim 1, wherein the lens comprises a synthetic polymeric material.

9. The method of claim 1, further comprising forming a plurality of incisions in the epithelium.

10. The method of claim 1, wherein the inserting step occurs substantially without damaging Bowman's membrane.

11. The method of claim 1, wherein the inserting step occurs substantially without damaging a portion of a stroma of the cornea of the eye.

12. The method of claim 1, further comprising administering a healing agent to the eye in an amount effective to promote healing of the epithelium.

13. The method of claim 1, further comprising forming an incision in the epithelium, and passing the lens through the incision.

14. The method of claim 13, wherein the epithelium is lifted using a vacuum.

15. The method of claim 13, wherein the epithelium is lifted by delivering a fluid beneath the epithelium.

16. The method of claim 1, further comprising applying an effective amount of an epithelium preserving agent to the epithelium.

17. The method of claim 16, wherein the epithelium preserving agent includes a gel.

18. The method of claim 16 wherein the epithelium preserving agent comprises a component selected from the group consisting of water soluble polymeric materials, water swellable polymeric materials and mixtures thereof.

19. The method of claim 16, wherein the epithelium preserving agent includes at least one cellulosic component.

20. The method of claim 19, wherein the epithelium preserving agent includes hydroxymethylcellulose.

21. The method of claim 1, further comprising creating the pocket using a sharp blade to slice through the epithelium.

22. The method of claim 1, further comprising creating the pocket using a blunt instrument to separate the epithelium substantially without slicing the epithelium.

23. The method of claim 1, wherein the creating step comprises using a microkeratome.

24. The method of claim 22, wherein the blunt instrument is a spatula or a wire.

25. The method of claim 15, wherein the fluid includes sodium chloride or other tonicity agent.

26. The method of claim 15, wherein the fluid is a hypertonic aqueous liquid.

27. The method of claim 1, further comprising:
applying a liquid to the corneal epithelium, the liquid being effective in loosening the epithelium substantially without killing epithelial cells;
treating the epithelium to provide or maintain the epithelium in a moisturized state;
wherein the epithelial cell layer is separated by raising a portion of the loosened, moisturized epithelium from the Bowman's membrane located below the epithelium; and
forming one or more incisions in the raised portion of the epithelium to accommodate the lens.

28. The method of claim 27, wherein the steps occur sequentially.

29. The method of claim 27, further comprising, prior to the forming step, delivering a substance beneath the raised portion of the corneal epithelium to maintain a spaced apart relationship between the epithelium and Bowman's membrane.

30. The method of claim 27, wherein the liquid that is applied includes sodium chloride or other tonicity agent.

31. The method of claim 27 wherein the liquid that is applied is a hypertonic aqueous liquid.

32. The method of claim 27, further comprising scoring a portion of the epithelium to create an epithelial defect prior to applying the liquid.

33. The method of claim 27, wherein the treating step comprises applying a gel to the epithelium.

34. The method of claim 33, wherein the gel-containing composition comprises a component selected from the group consisting of water soluble polymeric materials, water swellable polymeric materials and mixtures thereof.

35. The method of claim 33, wherein the gel-containing composition comprises at least one cellulosic component.

36. The method of claim 35 wherein the gel-containing composition comprises hydroxymethylcellulose.

37. The method of claim 27, wherein the step of separating the epithelium from the Bowman's membrane includes using a blunt dissection apparatus.

38. The method of claim 27, wherein the substance that is delivered to beneath the raised portion of the epithelium is a gel-containing composition.

39. The method of claim 38, wherein the gel-containing composition comprises a component selected from the group consisting of water soluble polymeric materials, water swellable polymeric materials and mixtures thereof.

40. The method of claim 38, wherein the gel-containing composition comprises a cellulosic component.

41. The method of claim 38, wherein the gel-containing composition includes hydroxymethylcellulose.

42. The method of claim 27, wherein the forming step comprises forming a plurality of incisions in the raised portion of the epithelium.

43. The method of claim 1, further comprising administering a moisturizer to the epithelium effective in providing and/or maintaining the epithelium in a moisturized state.

44. The method of claim 1, further comprising:
    applying a liquid to the corneal epithelium, the liquid being effective in loosening the epithelium substantially without killing epithelial cells;
    wherein the epithelial cell layer is separated by raising a portion of the loosened epithelium from the Bowman's membrane located below the epithelium;
    delivering a substance beneath the raised portion of the epithelium to maintain a spaced apart relationship between the epithelium and the surface of the cornea;
    forming one or more elongated incisions in the raised portion of the epithelium to accommodate the lens.

45. The method of claim 44, wherein the liquid that is applied includes sodium chloride or other tonicity agent.

46. The method of claim 44, wherein the liquid that is applied is a hypertonic aqueous liquid.

47. The method of claim 44, further comprising scoring a portion of the epithelium to create an epithelial defect prior to applying the liquid.

48. The method of claim 44, wherein the step of raising a portion of the epithelium includes using a vacuum.

49. The method of claim 44, wherein the step of separating the epithelium from the surface of the cornea includes using a blunt dissection apparatus.

50. The method of claim 49, wherein the blunt dissection apparatus comprises a spatula or a wire.

51. The method of claim 44, wherein the substance that is delivered to beneath the raised portion of the epithelium is a gel-containing composition.

52. The method of claim 51, wherein the gel-containing composition comprises a component selected from the group consisting of water soluble polymeric materials, water swellable polymeric materials and mixtures thereof.

53. The method of claim 51, wherein the gel-containing composition comprises at least one cellulosic component.

54. The method of claim 53, wherein the gel-containing composition includes hydroxymethylcellulose.

55. The method of claim 44, wherein the one or more incisions are formed using a microkeratome.

56. The method of claim 44, wherein the forming step comprises forming a plurality of incisions in the raised portion of the epithelium.

57. The method of claim 44, further comprising applying a healing agent to the epithelium at the one or more incisions.

58. The method of claim 1, further comprising applying an aqueous fluid to the eye.

59. The method of claim 58, wherein the aqueous fluid is selected from the group consisting of water and saline.

60. The method of claim 58, further comprising cooling the corneal epithelium.

61. The method of claim 1, wherein a biodegradable adhesive is applied to the epithelium and wherein the lens forms a natural bond to the Bowman's membrane.

62. The method of claim 1, wherein the lens comprises a cellular attachment element.

63. The method of claim 1, wherein the lens comprises an agent selected from the group consisting of growth factors, extracellular matrix proteins, fragments thereof, and combinations thereof.

64. The method of claim 1, wherein the lens comprises collagen.

65. The method of claim 1, wherein the lens comprises recombinant collagen.

66. The method of claim 1, wherein the lens comprises collagen and a synthetic polymeric material.

67. The method of claim 1, wherein the lens is free of donor corneal tissue.

68. The method of claim 1, wherein the lens comprises collagen Type I.

69. The method of claim 1, wherein the lens comprises collagen other than collagen Type I.

70. The method of claim 27, wherein the forming step comprises applying a fluid to the corneal epithelium.

71. The method of claim 27, wherein the forming step comprises applying a chemical to the corneal epithelium.

72. A method for vision correction of an eye having a corneal epithelium and a Bowman's membrane disposed under the corneal epithelium, the method comprising:
    cooling the corneal epithelium of eye;
    separating the corneal epithelium from the Bowman's membrane to form an epithelial cell layer separated from the Bowman's membrane and a pocket extending between the epithelial cell layer and the Bowman's membrane, the epithelial cell layer separated from the Bowman's membrane having a periphery substantially attached to the Bowman's membrane to fix a lens to the eye with the corneal epithelial layer; and
    inserting a lens into the pocket between the epithelial cell layer and the Bowman's membrane of the eye, such that the lens is substantially fixed on the Bowman's membrane with the epithelial cell layer.

73. The method of claim 72, wherein the cooling is effective in protecting corneal epithelial cells of the corneal epithelium from cellular injury resulting from creation of the pocket.

74. The method of claim 72, wherein the pocket is created using a separator, and the separator is cooled to cool the corneal epithelium.

75. The method of claim 72, further comprising applying an aqueous liquid to the eye.

76. The method of claim 75, wherein the aqueous liquid is selected from the group consisting of water and saline.

77. The method of claim 72, wherein a biodegradable adhesive is applied to the epithelium and wherein the lens forms a natural bond to the Bowman's membrane.

78. The method of claim 72, wherein the lens comprises collagen.

79. The method of claim 72, wherein the lens comprises recombinant collagen.

80. The method of claim 72, wherein the lens comprises a synthetic polymeric material.

81. The method of claim 72, wherein the lens comprises collagen and a synthetic polymeric material.

82. The method of claim 72, wherein the lens is free of donor corneal tissue.

83. The method of claim 72, wherein the lens comprises collagen Type I.

84. The method of claim 72, wherein the lens comprises collagen other than collagen Type I.

85. The method of claim 72, wherein the lens comprises a cellular attachment element.

86. The method of claim 72, wherein the lens comprises an agent selected from the group consisting of growth factors, extracellular matrix proteins, fragments thereof, and combinations thereof.

87. The method of claim 72, further comprising creating the pocket using a microkeratome.

88. A method for vision correction of an eye having a corneal epithelium and a Bowman's membrane disposed under the corneal epithelium, the method comprising:
separating the corneal epithelium from the Bowman's membrane to form an epithelial cell layer separated from the Bowman's membrane and a pocket extending between the epithelial cell layer and the Bowman's membrane, the epithelial cell layer separated from the Bowman's membrane having a periphery substantially attached to the Bowman's membrane to fix a lens on the Bowman's membrane with the corneal epithelial layer;
inserting the lens into the pocket between the epithelial cell layer and the Bowman's membrane of the eye, such that the lens is substantially fixed to the eye with the epithelial cell layer; and
applying an effective amount of an epithelium preserving agent to the epithelium, wherein the epithelium preserving agent includes at least one cellulosic component.

89. The method of claim 88, wherein the epithelium preserving agent includes hydroxymethylcellulose.

90. A method for vision correction of an eye having a corneal epithelium and a Bowman's membrane disposed under the corneal epithelium, the method, comprising:
applying a liquid to the corneal epithelium of the eye, the liquid being effective in loosening the epithelium substantially without killing epithelial cells;
treating the epithelium to provide or maintain the epithelium in a moisturized state, wherein the treating step comprises applying a gel containing composition to the epithelium;
raising a portion of the loosened, moisturized epithelium to separate the portion of the corneal epithelium from the Bowman's membrane to form an epithelial cell layer separated from the Bowman's membrane and a pocket, the pocket extending between the epithelial cell layer and the Bowman's membrane, the epithelial cell layer separated from the Bowman's membrane having a periphery substantially attached to the Bowman's membrane to fix a lens to the eye;
forming one or more incisions in the raised portion of the epithelium to access the pocket between the corneal epithelium and Bowman's membrane; and
inserting a lens into the pocket through the one or more incisions such that the lens is substantially fixed on the Bowman's membrane of the eye with the epithelial cell layer.

91. The method of claim 90, wherein the gel-containing composition comprises a component selected from the group consisting of water soluble polymeric materials, water swellable polymeric materials and mixtures thereof.

92. The method of claim 90, wherein the gel-containing composition comprises at least one cellulosic component.

93. The method of claim 92, wherein the gel-containing composition comprises hydroxymethylcellulose.

94. A method for vision correction of an eye having a corneal epithelium and a Bowman's membrane disposed under the corneal epithelium, the method comprising:
applying a liquid to a corneal epithelium of an eye, the liquid being effective in loosening the epithelium substantially without killing epithelial cells;
raising a portion of the loosened, moisturized epithelium to separate the portion of the corneal epithelium from the Bowman's membrane to form an epithelial cell layer separated from the Bowman's membrane and a pocket, the pocket extending between the epithelial cell layer and the Bowman's membrane, the epithelial cell layer separated from the Bowman's membrane having a periphery substantially attached to the Bowman's membrane to fix a lens to the eye;
delivering, a gel-containing composition beneath the raised portion of the epithelium to maintain a spaced apart relationship between the epithelial cell layer and the Bowman's membrane surface of the cornea;
forming one or more elongated incisions in the raised portion of the epithelium to access the pocket between the corneal epithelium and Bowman's membrane; and
inserting a lens into the pocket through the one or more incisions such that the lens is substantially fixed on the Bowman's membrane of the eye with the epithelial cell layer.

95. The method of claim 94, wherein the gel-containing composition comprises a component selected from the group consisting of water soluble polymeric materials, water swellable polymeric materials and mixtures thereof.

96. The method of claim 94, wherein the gel-containing composition comprises at least one cellulosic component.

97. The method of claim 96, wherein the gel-containing composition includes hydroxymethylcellulose.

98. The method of claim 1 wherein the lens forms a natural bond with the Bowman's membrane to hold the lens in place.

99. The method of claim 98 wherein an adhesive is applied to the epithelium.

100. The method of claim 1 further comprising forming an incision in the epithelium and wherein the lens is inserted into the pocket through the incision.

101. The method of claim 100 wherein the incision comprises an incision size and the pocket comprises a pocket size, and wherein the incision size is less than the pocket size.

102. The method of claim 101 wherein the lens is deformed to fit through the incision when the lens is inserted into the pocket and wherein the lens is at least one of folded or rolled to deform the lens to fit through the incision.

103. The method of claim 1 wherein the lens comprises an edge configured to promote epithelial cell migration over the edge of the lens.

104. The method of claim 103 wherein the edge comprise a thickness less than about 30 micrometers to promote epithelial cell migration over the edge of the lens.

105. The method of claim 103 wherein the lens comprises an anterior surface and a posterior surface, the edge comprising a rounded portion of the anterior surface and an apex along the posterior surface to promote the epithelial cell migration.

106. The method of claim 1 wherein the lens is configured to correct astigmatism of the eye and wherein the lens is held in a fixed position by the epithelium to maintain an orientation of the lens on the eye.

107. The method of claim 1 wherein the lens is configured to correct aberration of the eye and wherein the lens is held in a fixed position by the epithelium to maintain an orientation of the lens on the eye.

108. The method of claim 107 wherein the aberration comprises an asymmetrical higher-order wavefront aberration and wherein the lens is configured to maintain a desired orientation to correct the higher-order asymmetrical wavefront aberration.

109. The method of claim 1 wherein the lens is configured to correct presbyopia of the eye and wherein the lens is held in a fixed position by the epithelium to maintain correct the presbyopia of the eye.

* * * * *